US00RE43399E

(19) United States
(12) Reissued Patent
Simpson et al.

(10) Patent Number: US RE43,399 E
(45) Date of Reissued Patent: May 22, 2012

(54) ELECTRODE SYSTEMS FOR ELECTROCHEMICAL SENSORS

(75) Inventors: Peter C. Simpson, Encinitas, CA (US); James R. Petisce, San Clemente, CA (US); Victoria E. Carr-Brendel, Edina, MN (US); James H. Brauker, Addison, MI (US)

(73) Assignee: DexCom, Inc., San Diego, CA (US)

(21) Appl. No.: 12/139,305

(22) Filed: Jun. 13, 2008

Related U.S. Patent Documents

Reissue of:
(64) Patent No.: 7,074,307
Issued: Jul. 11, 2006
Appl. No.: 10/897,312
Filed: Jul. 21, 2004

U.S. Applications:
(60) Provisional application No. 60/490,007, filed on Jul. 25, 2003.

(51) Int. Cl.
*G01N 27/327* (2006.01)
*A61B 5/05* (2006.01)

(52) U.S. Cl. ..... 204/403.05; 204/403.11; 600/345; 600/347

(58) Field of Classification Search ..... 204/403.01–403.15; 205/777.5, 205/778, 792; 600/345–347
See application file for complete search history.

(56) References Cited

U.S. PATENT DOCUMENTS

| | | | |
|---|---|---|---|
| 1,564,641 | A | 12/1925 | St. James |
| 2,402,306 | A | 6/1946 | Turkel |
| 3,210,578 | A | 10/1965 | Sherer |
| 3,381,371 | A | 5/1968 | Russell |
| 3,775,182 | A | 11/1973 | Patton et al. |
| 3,826,244 | A | 7/1974 | Salcman et al. |
| 3,838,033 | A | 9/1974 | Mindt et al. |
| 3,933,593 | A | 1/1976 | Sternberg |
| 3,982,530 | A | 9/1976 | Storch |
| 4,052,754 | A | 10/1977 | Homsy |

(Continued)

FOREIGN PATENT DOCUMENTS

| | | |
|---|---|---|
| EP | 0 098 592 | 1/1984 |

(Continued)

OTHER PUBLICATIONS

Armour, et al. Dec. 1990. Application of Chronic Intravascular Blood Glucose Sensor in Dogs. Diabetes 39:1519-1526.

(Continued)

*Primary Examiner* — Alex Noguerola
(74) *Attorney, Agent, or Firm* — Knobbe Martens Olson & Bear LLP

(57) ABSTRACT

The present invention relates generally to systems and methods for improved electrochemical measurement of analytes. The preferred embodiments employ electrode systems including an analyte-measuring electrode for measuring the analyte or the product of an enzyme reaction with the analyte and an auxiliary electrode configured to generate oxygen and/or reduce electrochemical interferants. Oxygen generation by the auxiliary electrode advantageously improves oxygen availability to the enzyme and/or counter electrode; thereby enabling the electrochemical sensors of the preferred embodiments to function even during ischemic conditions. Interferant modification by the auxiliary electrode advantageously renders them substantially non-reactive at the analyte-measuring electrode, thereby reducing or eliminating inaccuracies in the analyte signal due to electrochemical interferants.

152 Claims, 4 Drawing Sheets

U.S. PATENT DOCUMENTS

| | | | | |
|---|---|---|---|---|
| 4,067,322 | A | | 1/1978 | Johnson |
| 4,197,840 | A | | 4/1980 | Beck et al. |
| 4,240,889 | A | | 12/1980 | Yoda et al. |
| 4,255,500 | A | | 3/1981 | Hooke |
| 4,324,257 | A | | 4/1982 | Albarda et al. |
| 4,374,013 | A | * | 2/1983 | Enfors ..... 204/403.12 |
| 4,378,016 | A | | 3/1983 | Loeb |
| 4,388,166 | A | | 6/1983 | Suzuki et al. |
| 4,402,694 | A | | 9/1983 | Ash et al. |
| 4,418,148 | A | | 11/1983 | Oberhardt |
| 4,431,004 | A | | 2/1984 | Bessman et al. |
| 4,431,507 | A | * | 2/1984 | Nankai et al. ..... 204/403.11 |
| 4,442,841 | A | | 4/1984 | Uehara et al. |
| 4,477,314 | A | | 10/1984 | Richter et al. |
| 4,484,987 | A | | 11/1984 | Gough |
| 4,494,950 | A | | 1/1985 | Fischell |
| RE31,916 | E | | 6/1985 | Oswin et al. |
| 4,545,382 | A | | 10/1985 | Higgins et al. |
| 4,571,292 | A | | 2/1986 | Liu et al. |
| 4,578,215 | A | | 3/1986 | Bradley |
| 4,650,547 | A | | 3/1987 | Gough |
| 4,655,880 | A | | 4/1987 | Liu |
| 4,671,288 | A | | 6/1987 | Gough |
| 4,672,970 | A | | 6/1987 | Uchida et al. |
| 4,680,268 | A | | 7/1987 | Clark, Jr. |
| 4,685,463 | A | | 8/1987 | Williams |
| 4,703,756 | A | | 11/1987 | Gough et al. |
| 4,711,245 | A | | 12/1987 | Higgins |
| 4,721,677 | A | | 1/1988 | Clark, Jr. |
| 4,726,381 | A | | 2/1988 | Jones |
| 4,750,496 | A | | 6/1988 | Reinhart et al. |
| 4,757,022 | A | | 7/1988 | Shults et al. |
| 4,763,658 | A | | 8/1988 | Jones |
| 4,776,944 | A | | 10/1988 | Janata et al. |
| 4,781,798 | A | | 11/1988 | Gough |
| 4,786,657 | A | | 11/1988 | Hammar et al. |
| 4,795,542 | A | | 1/1989 | Ross et al. |
| 4,813,424 | A | | 3/1989 | Wilkins |
| 4,822,336 | A | | 4/1989 | DiTraglia |
| 4,858,615 | A | | 8/1989 | Meinema |
| 4,861,830 | A | | 8/1989 | Ward, Jr. |
| 4,871,440 | A | | 10/1989 | Nagata et al. |
| 4,883,057 | A | | 11/1989 | Broderick |
| 4,886,740 | A | | 12/1989 | Vadgama |
| 4,890,620 | A | | 1/1990 | Gough |
| 4,890,621 | A | | 1/1990 | Hakky |
| 4,909,908 | A | | 3/1990 | Ross et al. |
| 4,919,141 | A | | 4/1990 | Zier et al. |
| 4,927,407 | A | | 5/1990 | Dorman |
| 4,953,552 | A | | 9/1990 | DeMarzo |
| 4,955,861 | A | | 9/1990 | Enegren et al. |
| 4,970,145 | A | | 11/1990 | Bennetto et al. |
| 4,973,320 | A | | 11/1990 | Brenner et al. |
| 4,974,929 | A | | 12/1990 | Curry |
| 4,975,175 | A | | 12/1990 | Karube et al. |
| 4,992,794 | A | | 2/1991 | Brouwers |
| 4,994,167 | A | | 2/1991 | Shults et al. |
| 5,030,333 | A | | 7/1991 | Clark, Jr. |
| 5,034,112 | A | | 7/1991 | Murase et al. |
| 5,050,612 | A | | 9/1991 | Matsumura |
| 5,063,081 | A | | 11/1991 | Cozzette et al. |
| 5,089,112 | A | | 2/1992 | Skotheim et al. |
| 5,140,985 | A | | 8/1992 | Schroeder et al. |
| 5,155,149 | A | | 10/1992 | Atwater et al. |
| 5,165,407 | A | | 11/1992 | Wilson et al. |
| 5,171,689 | A | | 12/1992 | Kawaguri et al. |
| 5,183,549 | A | | 2/1993 | Joseph et al. |
| 5,190,041 | A | | 3/1993 | Palti |
| 5,198,771 | A | | 3/1993 | Fidler et al. |
| 5,200,051 | A | | 4/1993 | Cozzette et al. |
| 5,202,261 | A | | 4/1993 | Musho et al. |
| 5,212,050 | A | | 5/1993 | Mier et al. |
| 5,242,835 | A | | 9/1993 | Jensen |
| 5,249,576 | A | | 10/1993 | Goldberger et al. |
| 5,250,439 | A | | 10/1993 | Musho et al. |
| 5,266,179 | A | | 11/1993 | Nankai et al. |
| 5,281,319 | A | | 1/1994 | Kaneko et al. |
| 5,282,848 | A | | 2/1994 | Schmitt |
| 5,284,140 | A | | 2/1994 | Allen et al. |
| 5,286,364 | A | | 2/1994 | Yacynych et al. |
| 5,298,144 | A | | 3/1994 | Spokane |
| 5,299,571 | A | | 4/1994 | Mastrototaro |
| 5,307,263 | A | | 4/1994 | Brown |
| 5,310,469 | A | | 5/1994 | Cunningham et al. |
| 5,312,361 | A | | 5/1994 | Zadini et al. |
| 5,322,063 | A | | 6/1994 | Allen et al. |
| 5,330,634 | A | | 7/1994 | Wong et al. |
| 5,337,747 | A | | 8/1994 | Neftel |
| 5,352,348 | A | | 10/1994 | Young et al. |
| 5,352,351 | A | | 10/1994 | White |
| 5,354,449 | A | | 10/1994 | Band et al. |
| 5,372,133 | A | | 12/1994 | Hogen Esch |
| 5,384,028 | A | | 1/1995 | Ito |
| 5,387,327 | A | | 2/1995 | Khan |
| 5,390,671 | A | | 2/1995 | Lord et al. |
| 5,391,250 | A | | 2/1995 | Cheney, II et al. |
| 5,411,647 | A | | 5/1995 | Johnson et al. |
| 5,411,866 | A | | 5/1995 | Luong |
| 5,425,717 | A | | 6/1995 | Mohiuddin |
| 5,428,123 | A | | 6/1995 | Ward et al. |
| 5,431,160 | A | | 7/1995 | Wilkins |
| 5,438,984 | A | | 8/1995 | Schoendorfer |
| 5,462,645 | A | | 10/1995 | Albery et al. |
| 5,466,575 | A | | 11/1995 | Cozzette et al. |
| 5,469,846 | A | | 11/1995 | Khan |
| 5,474,552 | A | | 12/1995 | Palti |
| 5,476,094 | A | | 12/1995 | Allen et al. |
| 5,476,776 | A | | 12/1995 | Wilkins |
| 5,482,008 | A | | 1/1996 | Stafford et al. |
| 5,482,473 | A | | 1/1996 | Lord et al. |
| 5,486,776 | A | | 1/1996 | Chiang |
| 5,494,562 | A | | 2/1996 | Maley et al. |
| 5,496,453 | A | | 3/1996 | Uenoyama et al. |
| 5,497,772 | A | | 3/1996 | Schulman et al. |
| 5,502,396 | A | | 3/1996 | Desarzens et al. |
| 5,507,288 | A | | 4/1996 | Bocker et al. |
| 5,508,509 | A | | 4/1996 | Yafuso et al. |
| 5,531,878 | A | | 7/1996 | Vadgama et al. |
| 5,564,439 | A | | 10/1996 | Picha |
| 5,568,806 | A | | 10/1996 | Cheney, II et al. |
| 5,569,186 | A | | 10/1996 | Lord et al. |
| 5,569,462 | A | | 10/1996 | Martinson et al. |
| 5,571,395 | A | | 11/1996 | Park et al. |
| 5,575,930 | A | | 11/1996 | Tietje-Girault et al. |
| 5,582,184 | A | | 12/1996 | Erickson et al. |
| 5,582,497 | A | | 12/1996 | Noguchi |
| 5,593,852 | A | | 1/1997 | Heller et al. |
| 5,605,152 | A | | 2/1997 | Slate et al. |
| 5,607,565 | A | | 3/1997 | Azarnia et al. |
| 5,611,900 | A | | 3/1997 | Worden |
| 5,624,537 | A | | 4/1997 | Turner et al. |
| 5,628,890 | A | | 5/1997 | Carter et al. |
| 5,640,954 | A | | 6/1997 | Pfeiffer |
| 5,653,863 | A | | 8/1997 | Genshaw et al. |
| 5,660,163 | A | | 8/1997 | Schulman et al. |
| 5,665,222 | A | | 9/1997 | Heller et al. |
| 5,676,820 | A | | 10/1997 | Wang et al. |
| 5,682,884 | A | | 11/1997 | Hill |
| 5,686,829 | A | | 11/1997 | Girault |
| 5,703,359 | A | | 12/1997 | Wampler, III |
| 5,704,354 | A | | 1/1998 | Preidel et al. |
| 5,706,807 | A | | 1/1998 | Picha |
| 5,707,502 | A | | 1/1998 | McCaffrey et al. |
| 5,711,861 | A | | 1/1998 | Ward et al. |
| 5,735,273 | A | | 4/1998 | Kurnik et al. |
| 5,741,330 | A | | 4/1998 | Brauker et al. |
| 5,741,634 | A | | 4/1998 | Nozoe et al. |
| 5,746,898 | A | | 5/1998 | Preidel |
| 5,749,832 | A | | 5/1998 | Vadgama et al. |
| 5,756,632 | A | | 5/1998 | Ward et al. |
| 5,776,324 | A | | 7/1998 | Usala |
| 5,777,060 | A | | 7/1998 | Van Antwerp |
| 5,791,344 | A | | 8/1998 | Schulman et al. |
| 5,795,453 | A | | 8/1998 | Gilmartin |
| 5,795,774 | A | | 8/1998 | Matsumoto et al. |
| 5,800,420 | A | | 9/1998 | Gross |
| 5,807,375 | A | | 9/1998 | Gross et al. |

5,820,622 A 10/1998 Gross et al.
5,833,603 A 11/1998 Kovacs et al.
5,837,454 A 11/1998 Cozzette et al.
5,840,148 A 11/1998 Campbell et al.
5,851,197 A 12/1998 Marano et al.
5,863,400 A 1/1999 Drummond et al.
5,879,373 A 3/1999 Roper et al.
5,882,494 A 3/1999 Van Antwerp
5,895,235 A 4/1999 Droz
5,914,026 A 6/1999 Blubaugh, Jr. et al.
5,928,130 A 7/1999 Schmidt
5,944,661 A 8/1999 Swette et al.
5,954,643 A 9/1999 VanAntwerp et al.
5,954,954 A 9/1999 Houck et al.
5,957,854 A 9/1999 Besson et al.
5,963,132 A 10/1999 Yoakum
5,964,993 A 10/1999 Blubaugh et al.
5,965,380 A 10/1999 Heller et al.
5,972,199 A 10/1999 Heller
5,985,129 A 11/1999 Gough et al.
5,989,409 A 11/1999 Kurnik et al.
5,999,848 A 12/1999 Gord et al.
6,001,067 A 12/1999 Shults et al.
6,011,984 A 1/2000 Van Antwerp et al.
6,013,113 A 1/2000 Mika
6,030,827 A 2/2000 Davis et al.
6,049,727 A 4/2000 Crothall
6,051,389 A 4/2000 Ahl et al.
6,059,946 A 5/2000 Yukawa et al.
6,066,083 A 5/2000 Slater et al.
6,066,448 A * 5/2000 Wohlstadter et al. ..... 435/6
6,081,735 A 6/2000 Diab et al.
6,081,736 A 6/2000 Colvin et al.
6,083,710 A 7/2000 Heller et al.
6,088,608 A 7/2000 Schulman et al.
6,093,156 A 7/2000 Cunningham et al.
6,093,172 A 7/2000 Funderburk et al.
6,117,290 A 9/2000 Say
6,119,028 A 9/2000 Schulman et al.
6,120,676 A 9/2000 Heller et al.
6,121,009 A 9/2000 Heller et al.
6,122,536 A 9/2000 Sun et al.
6,134,461 A 10/2000 Say et al.
6,141,573 A 10/2000 Kurnik et al.
6,144,869 A 11/2000 Berner et al.
6,144,871 A 11/2000 Saito et al.
6,162,611 A 12/2000 Heller et al.
6,175,752 B1 1/2001 Say et al.
6,189,536 B1 2/2001 Martinez et al.
6,212,416 B1 4/2001 Ward et al.
6,233,471 B1 5/2001 Berner et al.
6,248,067 B1 6/2001 Causey, III et al.
6,256,522 B1 7/2001 Schultz
6,259,937 B1 7/2001 Schulman et al.
6,264,825 B1 * 7/2001 Blackburn et al. ..... 205/777.5
6,268,161 B1 7/2001 Han et al.
6,274,285 B1 8/2001 Gries et al.
6,275,717 B1 8/2001 Gross et al.
6,284,478 B1 9/2001 Heller et al.
6,285,897 B1 9/2001 Kilcoyne et al.
6,293,925 B1 9/2001 Safabash et al.
6,294,281 B1 9/2001 Heller
6,300,002 B1 10/2001 Webb et al.
6,309,526 B1 10/2001 Fujiwara et al.
6,325,979 B1 12/2001 Hahn et al.
6,329,161 B1 12/2001 Heller et al.
6,343,225 B1 1/2002 Clark, Jr.
6,356,776 B1 3/2002 Berner et al.
6,360,888 B1 3/2002 Melver et al.
6,366,794 B1 4/2002 Moussy et al.
6,368,141 B1 4/2002 VanAntwerp et al.
6,368,274 B1 4/2002 Van Antwerp et al.
6,400,974 B1 6/2002 Lesho
6,407,195 B2 6/2002 Sherman et al.
6,409,674 B1 6/2002 Brockway et al.
6,413,393 B1 7/2002 Van Antwerp et al.
6,418,332 B1 7/2002 Mastrototaro et al.
6,424,847 B1 7/2002 Mastrototaro et al.
6,442,413 B1 8/2002 Silver
6,447,448 B1 9/2002 Ishikawa et al.
6,454,710 B1 9/2002 Ballerstadt et al.
6,459,917 B1 10/2002 Gowda et al.
6,461,496 B1 10/2002 Feldman et al.
6,466,810 B1 10/2002 Ward et al.
6,484,045 B1 11/2002 Holker et al.
6,484,046 B1 11/2002 Say et al.
6,498,941 B1 12/2002 Jackson
6,510,329 B2 1/2003 Heckel
6,512,939 B1 1/2003 Colvin et al.
6,514,718 B2 2/2003 Heller et al.
6,520,326 B2 2/2003 McIvor et al.
6,534,711 B1 3/2003 Pollack
6,542,765 B1 4/2003 Guy et al.
6,546,268 B1 4/2003 Ishikawa et al.
6,547,839 B2 4/2003 Zhang et al.
6,551,496 B1 4/2003 Moles et al.
6,553,241 B2 4/2003 Mannheimer et al.
6,558,320 B1 5/2003 Causey
6,558,321 B1 5/2003 Burd et al.
6,558,351 B1 5/2003 Steil et al.
6,560,471 B1 5/2003 Heller et al.
6,565,509 B1 5/2003 Say et al.
6,579,498 B1 6/2003 Eglise
6,595,919 B2 7/2003 Berner et al.
6,612,984 B1 9/2003 Kerr
6,613,379 B2 9/2003 Ward et al.
6,615,078 B1 9/2003 Burson et al.
6,618,934 B1 9/2003 Feldman et al.
6,642,015 B2 11/2003 Vachon et al.
6,654,625 B1 11/2003 Say et al.
6,689,265 B2 2/2004 Heller et al.
6,699,383 B2 3/2004 Lemire et al.
6,702,857 B2 3/2004 Brauker et al.
6,721,587 B2 4/2004 Gough
6,730,200 B1 5/2004 Stewart et al.
6,737,158 B1 5/2004 Thompson
6,741,877 B1 5/2004 Shults et al.
6,743,635 B2 6/2004 Neel et al.
6,773,565 B2 8/2004 Kunimoto et al.
6,784,274 B2 8/2004 van Antwerp et al.
6,793,802 B2 9/2004 Lee et al.
6,801,041 B2 10/2004 Karinka et al.
6,802,957 B2 10/2004 Jung et al.
6,809,507 B2 10/2004 Morgan et al.
6,809,653 B1 10/2004 Mann et al.
6,862,465 B2 3/2005 Shults et al.
6,881,551 B2 4/2005 Heller et al.
6,891,317 B2 5/2005 Pei et al.
6,892,085 B2 5/2005 McIvor et al.
6,893,552 B1 5/2005 Wang et al.
6,895,263 B2 5/2005 Shin et al.
6,895,265 B2 5/2005 Silver
6,952,604 B2 10/2005 DeNuzzio et al.
6,965,791 B1 11/2005 Hitchcock et al.
6,972,080 B1 12/2005 Tomioka et al.
7,003,336 B2 2/2006 Holker et al.
7,008,979 B2 3/2006 Schottman et al.
7,033,322 B2 4/2006 Silver
7,070,580 B2 7/2006 Nielsen
7,078,582 B2 7/2006 Stebbings et al.
7,081,195 B2 7/2006 Simpson et al.
7,110,803 B2 9/2006 Shults et al.
7,115,884 B1 10/2006 Walt et al.
7,134,999 B2 11/2006 Brauker et al.
7,136,689 B2 11/2006 Shults et al.
7,153,265 B2 12/2006 Vachon
7,166,074 B2 1/2007 Reghabit et al.
7,192,450 B2 3/2007 Brauker et al.
7,207,974 B2 4/2007 Safabash et al.
7,248,906 B2 7/2007 Dirac et al.
7,267,665 B2 9/2007 Steil et al.
7,279,174 B2 10/2007 Pacetti et al.
2002/0042561 A1 4/2002 Schulman et al.
2002/0084196 A1 7/2002 Liamos et al.
2002/0099997 A1 7/2002 Piret
2002/0119711 A1 8/2002 Van Antwerp et al.
2002/0177763 A1 11/2002 Burns et al.
2002/0188185 A1 12/2002 Sohrab 2003/0004457 A1 1/2003 Andersson
2003/0006669 A1 1/2003 Pei et al.
2003/0009093 A1 1/2003 Silver
2003/0032874 A1 2/2003 Rhodes et al.
2003/0036773 A1 2/2003 Whitehurst et al.
2003/0050546 A1 3/2003 Desai et al.
2003/0065254 A1 4/2003 Schulman et al.
2003/0088166 A1 5/2003 Say et al.
2003/0097082 A1 5/2003 Purdy et al.
2003/0125613 A1 7/2003 Enegren et al.
2003/0130616 A1 7/2003 Steil et al.
2003/0134347 A1 7/2003 Heller et al.
2003/0138674 A1 7/2003 Zeikus et al.
2003/0187338 A1 10/2003 Say et al.
2003/0199745 A1 10/2003 Burson et al.
2003/0203498 A1 10/2003 Neel et al.
2003/0211050 A1 11/2003 Majeti et al.
2003/0211625 A1 11/2003 Cohan
2003/0225324 A1 12/2003 Anderson et al.
2003/0225437 A1 12/2003 Ferguson
2003/0235817 A1 12/2003 Bartkowiak et al.
2004/0006263 A1 1/2004 Anderson et al.
2004/0015063 A1 1/2004 DeNuzzio et al.
2004/0045879 A1 3/2004 Shults et al.
2004/0063167 A1 4/2004 Kaastrup et al.
2004/0074785 A1 4/2004 Holker
2004/0078219 A1 4/2004 Kaylor
2004/0106857 A1 6/2004 Gough
2004/0106859 A1 6/2004 Say et al.
2004/0111017 A1 6/2004 Say et al.
2004/0133164 A1 7/2004 Funderburk et al.
2004/0138543 A1 7/2004 Russell et al.
2004/0143173 A1 7/2004 Reghabi et al.
2004/0167801 A1 8/2004 Say et al.
2004/0173472 A1 9/2004 Jung et al.
2004/0176672 A1 9/2004 Silver et al.
2004/0180391 A1 9/2004 Gratzl et al.
2004/0219664 A1 11/2004 Heller et al.
2004/0224001 A1 11/2004 Pacetti et al.
2004/0234575 A1 11/2004 Horres et al.
2004/0236200 A1 11/2004 Say et al.
2004/0242982 A1 12/2004 Sakata et al.
2004/0254433 A1 12/2004 Bandis
2005/0027180 A1 2/2005 Goode et al.
2005/0027181 A1 2/2005 Goode et al.
2005/0027182 A1 2/2005 Siddiqui et al.
2005/0027463 A1 2/2005 Goode et al.
2005/0031689 A1 2/2005 Shults et al.
2005/0033132 A1 2/2005 Shults et al.
2005/0038332 A1 2/2005 Saidara et al.
2005/0043598 A1 2/2005 Goode et al.
2005/0051427 A1 3/2005 Brauker et al.
2005/0051440 A1 3/2005 Simpson et al.
2005/0054909 A1 3/2005 Petisce et al.
2005/0056551 A1 3/2005 White et al.
2005/0056552 A1 3/2005 Simpson et al.
2005/0070770 A1 3/2005 Dirac et al.
2005/0077584 A1 4/2005 Uhland et al.
2005/0090607 A1 4/2005 Tapsak et al.
2005/0096519 A1 5/2005 DeNuzzio et al.
2005/0103625 A1 5/2005 Rhodes et al.
2005/0112169 A1 5/2005 Brauker et al.
2005/0115832 A1 6/2005 Simpson et al.
2005/0121322 A1 6/2005 Say
2005/0143635 A1 6/2005 Kamath et al.
2005/0176136 A1 8/2005 Burd et al.
2005/0177036 A1 8/2005 Shults et al.
2005/0181012 A1 8/2005 Saint et al.
2005/0182451 A1 8/2005 Griffin et al.
2005/0183954 A1 8/2005 Hitchcock et al.
2005/0192557 A1 9/2005 Brauker et al.
2005/0197554 A1 9/2005 Polcha
2005/0211571 A1 9/2005 Schulein et al.
2005/0215871 A1 9/2005 Feldman et al.
2005/0242479 A1 11/2005 Petisce et al.
2005/0245795 A1 11/2005 Goode et al.
2005/0245799 A1 11/2005 Brauker et al.
2005/0258037 A1 11/2005 Hajizadeh et al.
2005/0261563 A1 11/2005 Zhou et al.
2005/0272989 A1 12/2005 Shah et al.
2006/0003398 A1 1/2006 Heller et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020189 A1 1/2006 Brister et al.
2006/0020191 A1 1/2006 Brister et al.
2006/0020192 A1 1/2006 Brister et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0078908 A1 4/2006 Pitner et al.
2006/0079740 A1 4/2006 Silver et al.
2006/0142651 A1 6/2006 Brister et al.
2006/0155180 A1 7/2006 Brister et al.
2006/0177379 A1 8/2006 Asgari
2006/0183871 A1 8/2006 Ward et al.
2006/0183984 A1 8/2006 Dobbles et al.
2006/0183985 A1 8/2006 Brister et al.
2006/0189856 A1 8/2006 Petisce et al.
2006/0195029 A1 8/2006 Shults et al.
2006/0198864 A1 9/2006 Shults et al.
2006/0200019 A1 9/2006 Petisce et al.
2006/0200020 A1 9/2006 Brister et al.
2006/0200022 A1 9/2006 Brauker et al.
2006/0200970 A1 9/2006 Brister et al.
2006/0204536 A1 9/2006 Shults et al.
2006/0211921 A1 9/2006 Brauker et al.
2006/0222566 A1 10/2006 Brauker et al.
2006/0224108 A1 10/2006 Brauker et al.
2006/0229512 A1 10/2006 Petisce et al.
2006/0235285 A1 10/2006 Brister et al.
2006/0258761 A1 11/2006 Boock et al.
2006/0263839 A1 11/2006 Ward et al.
2006/0270922 A1 11/2006 Brauker et al.
2006/0270923 A1 11/2006 Brauker et al.
2006/0275857 A1 12/2006 Kjaer et al.
2006/0275859 A1 12/2006 Kjaer
2006/0289307 A1 12/2006 Yu et al.
2007/0007133 A1 1/2007 Mang et al.
2007/0027384 A1 2/2007 Brister et al.
2007/0027385 A1 2/2007 Brister et al.
2007/0032717 A1 2/2007 Brister et al.
2007/0032718 A1 2/2007 Shults et al.
2007/0038044 A1 2/2007 Dobbles et al.
2007/0045902 A1 3/2007 Brauker et al.
2007/0093704 A1 4/2007 Brister et al.
2007/0135698 A1 6/2007 Shah et al.
2007/0163880 A1 7/2007 Woo et al.
2007/0173709 A1 7/2007 Petisce et al.
2007/0173710 A1 7/2007 Petisce et al.
2007/0173711 A1 7/2007 Shah et al.
2007/0197889 A1 8/2007 Brister et al.
2007/0203966 A1 8/2007 Brauker et al.
2007/0208246 A1 9/2007 Brauker et al.
2007/0213611 A1 9/2007 Simpson et al.
2007/0215491 A1 9/2007 Heller et al.
2007/0218097 A1 9/2007 Heller et al.
2007/0227907 A1 10/2007 Shah et al.
2007/0232879 A1 10/2007 Brister et al.
2007/0235331 A1 10/2007 Simpson et al.
2007/0259217 A1 11/2007 Logan
2007/0275193 A1 11/2007 DeSimone et al.
2007/0299385 A1 12/2007 Santini et al.
2008/0021666 A1 1/2008 Goode et al.
2008/0027301 A1 1/2008 Ward et al.
2008/0033269 A1 2/2008 Zhang
2008/0034972 A1 2/2008 Gough et al.
2008/0045824 A1 2/2008 Tapsak et al.
2008/0154101 A1 6/2008 Goode et al.
2008/0188731 A1 8/2008 Brister et al.
2008/0194935 A1 8/2008 Brister et al.

| | | | |
|---|---|---|---|
| 2008/0194938 | A1 | 8/2008 | Brister et al. |
| 2008/0208025 | A1 | 8/2008 | Shults et al. |
| 2008/0214915 | A1 | 9/2008 | Brister et al. |
| 2008/0214918 | A1 | 9/2008 | Brister et al. |
| 2008/0242961 | A1 | 10/2008 | Brister et al. |
| 2008/0262334 | A1 | 10/2008 | Dunn et al. |
| 2008/0296155 | A1 | 12/2008 | Shults et al. |
| 2008/0306368 | A1 | 12/2008 | Goode et al. |
| 2009/0012379 | A1 | 1/2009 | Goode et al. |
| 2009/0045055 | A1 | 2/2009 | Rhodes et al. |
| 2009/0062633 | A1 | 3/2009 | Brauker et al. |
| 2009/0076356 | A1 | 3/2009 | Simpson et al. |
| 2009/0076360 | A1 | 3/2009 | Brister et al. |
| 2009/0099436 | A1 | 4/2009 | Brister et al. |
| 2009/0124879 | A1 | 5/2009 | Brister et al. |
| 2009/0143660 | A1 | 6/2009 | Brister et al. |

FOREIGN PATENT DOCUMENTS

| | | | |
|---|---|---|---|
| EP | 0 127 958 | | 12/1984 |
| EP | 0 284 518 | | 9/1988 |
| EP | 0 320 109 | | 6/1989 |
| EP | 0 353 328 | | 2/1990 |
| EP | 0 390 390 | | 10/1990 |
| EP | 0 396 788 | | 11/1990 |
| EP | 0 476 980 | | 3/1992 |
| EP | 0 534 074 | | 3/1993 |
| EP | 0 535 898 | | 4/1993 |
| EP | 0539625 | A1 | 5/1993 |
| EP | 0 817 809 | | 1/1998 |
| EP | 0 838 230 | | 4/1998 |
| EP | 0 967 788 | | 12/1999 |
| EP | 1153571 | A1 | 11/2001 |
| FR | 2 656 423 | | 6/1991 |
| FR | 2760962 | | 9/1998 |
| GB | 1 442 303 | | 7/1976 |
| JP | 62083649 | | 4/1987 |
| JP | 62083849 | | 4/1987 |
| JP | 63067560 | | 3/1988 |
| JP | 02002913 | | 1/1990 |
| JP | 3-293556 | | 12/1991 |
| JP | 2002-189015 | | 7/2002 |
| WO | WO 89/02720 | | 4/1989 |
| WO | WO 90/07575 | | 7/1990 |
| WO | WO 91/09302 | | 6/1991 |
| WO | WO 92/07525 | | 5/1992 |
| WO | WO 92/13271 | | 8/1992 |
| WO | WO 93/14693 | | 8/1993 |
| WO | WO 93/23744 | | 11/1993 |
| WO | WO 94/22367 | | 10/1994 |
| WO | WO 96/25089 | | 2/1995 |
| WO | WO 96/14026 | | 5/1996 |
| WO | WO 96/30431 | | 10/1996 |
| WO | WO 97/01986 | | 1/1997 |
| WO | WO 97/06727 | | 2/1997 |
| WO | WO 98/19159 | | 5/1998 |
| WO | WO 98/24358 | | 6/1998 |
| WO | WO 98/38906 | | 9/1998 |
| WO | WO 99/56613 | | 4/1999 |
| WO | WO 99/58051 | | 11/1999 |
| WO | WO 00/19887 | | 4/2000 |
| WO | WO 00/32098 | | 6/2000 |
| WO | WO 00/33065 | | 6/2000 |
| WO | WO 00/59373 | | 10/2000 |
| WO | WO 00/74753 | | 12/2000 |
| WO | WO 01/20019 | | 3/2001 |
| WO | WO 01/58348 | | 8/2001 |
| WO | WO 01/68901 | A2 | 9/2001 |
| WO | WO 01/88524 | A1 | 11/2001 |
| WO | WO 02/053764 | | 7/2002 |
| WO | WO 02/089666 | | 11/2002 |
| WO | WO 03/011131 | | 2/2003 |
| WO | WO 2004/021877 | A1 | 3/2004 |
| WO | WO 2005/012873 | | 2/2005 |
| WO | WO 2005/045394 | | 5/2005 |
| WO | WO 2005/057168 | | 6/2005 |
| WO | WO 2005/057175 | | 6/2005 |
| WO | WO 2005/026689 | | 10/2005 |
| WO | WO 2006/017358 | | 2/2006 |
| WO | WO 2006/018425 | | 2/2006 |
| WO | WO 2006/105146 | | 10/2006 |
| WO | WO 2007/114943 | | 10/2007 |

OTHER PUBLICATIONS

Aussedat, et al. 1997. A user-friendly method for calibrating a subcutaneous glucose sensor-based hypoglycaemic alarm. Biosensors & Bioelectronics 12(11):1061-1071.

Baker, et al. 1996. Dynamic delay and maximal dynamic error in continuous biosensors. Anal Chem 68(8):1292-1297.

Bani Amer, M. M. 2002. An accurate amperometric glucose sensor based glucometer with eliminated cross-sensitivity. J Med Eng Technol 26(5):208-213.

Bard et al. 1980. Electrochemical Methods. John Wiley & Sons, pp. 173-175.

Bode, B. W. 2000. Clinical utility of the continuous glucose monitoring system. Diabetes Technol Ther, 2(Suppl 1):S35-41.

Brooks, et al. "Development of an on-line glucose sensor for fermentation monitoring," Biosensors, 3:45-56 (1987/88).

Chia et al. 2004. Glucose sensors: toward closed loop insulin delivery. Endocrinol Metab Clin North Am 33:175-95.

Choleau, et al. 2002. Calibration of a subcutaneous amperometric glucose sensor implanted for 7 days in diabetic patients. Part 2. Superiority of the one-point calibration method. Biosensors and Bioelectronics 17:647-654.

Clark et al. 1987. Configurational cyclic voltammetry: increasing the specificity and reliablity of implanted electrodes, IEEE/Ninth Annual Conference of the Engineering in Medicine and Biology Society, pp. 0782-0783.

El Deheigy et al. 1986. Optimization of an implantable coated wire glucose sensor. J. Biomed Eng. 8: 121-129.

Fischer et al. 1995. Hypoglycaemia-warning by means of subcutaneous electrochemical glucose sensors: an animal study, Horm. Metab. Rese. 27:53.

Fischer et al. 1989. Oxygen Tension at the Subcutaneous Implantation Site of Glucose Sensors. Biomed. Biochem 11/12:965-972.

Frohnauer, et al. 2001. Graphical human insulin time-activity profiles using standardized definitions. Diabetes Technology & Therapeutics 3(3):419-429.

Frost, et al. 2002. Implantable chemical sensors for real-time clinical monitoring: Progress and challenges. Current Opinion in Chemical Biology 6:633-641.

Godsland, et al. 2001. Maximizing the Success Rate of Minimal Model Insulin Sensitivity Measurement in Humans: The Importance of Basal Glucose Levels. The Biochemical Society and the Medical Research Society, 1-9.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes Care, 17(5): 387-396.

Heller, "Electrical wiring of redox enzymes," Acc. Chem. Res., 23:128-134 (1990).

Johnson (1991). "Reproducible electrodeposition of biomolecules for the fabrication of miniature electroenzymatic biosensors," *Sensors and Actuators B,* 5:85-89.

Johnson et al. 1992. In vivo evaluation of an electroenzymatic glucose sensor implanted in subcutaneous tissue. Biosensors & Bioelectronics, 7:709-714.

Kerner, et al. "The function of a hydrogen peroxide-detecting electroenzymatic glucose electrode is markedly impaired in human sub-cutaneous tissue and plasma," Biosensors & Bioelectronics, 8:473-482 (1993).

Koschinsky, et al. 1998. New approach to technical and clinical evaluation of devices for self-monitoring of blood glucose. Diabetes Care 11(8): 619-619.

Mastrototaro, et al. "An electroenzymatic glucose sensor fabricated on a flexible substrate," Sensors and Actuators B, 5:139-44 (1991).

McKean, et al. Jul. 7, 1988. A Telemetry Instrumentation System for Chronically Implanted Glucose and Oxygen Sensors. Transactions on Biomedical Engineering 35:526-532.

Moatti-Sirat, D, et al. 1992. Evaluating in vitro and in vivo the interference of ascorbate and acetaminophen on glucose detection by a needle-type glucose sensor. Biosensors and Bioelectronics 7:345-352.
Moatti-Sirat et al., Reduction of acetaminophen interference in glucose sensors by a composite Nafion membrane: demonstration in rats and man, Diabetologia 37(6):610-616, Jun. 1994.
Pickup, et al. "Implantable glucose sensors: choosing the appropriate sensor strategy," *Biosensors,* 3:335-346 (1987/88).
Pickup, et al. "In vivo molecular sensing in diabetes mellitus: an implantable glucose sensor with direct electron transfer," Diabetologia, 32:213-217 (1989).
Pishko, et al. "Amperometric glucose microelectrodes prepared through immobilization of glucose oxidase in redox hydrogels," Anal. Chem., 63:2268-72 (1991).
Poitout, et al. 1993. A glucose monitoring system for on line estimation in man of blood glucose concentration using a miniaturized glucose sensor implanted in the subcutaneous tissue and a wearable control unit. Diabetologia 36:658-663.
Rebrin, et al. "Automated feedback control of subcutaneous glucose concentration in diabetic dogs," Diabetologia, 32:573-76 (1989).
Shaw, et al. "In vitro testing of a simply constructed, highly stable glucose sensor suitable for implantation in diabetic patients," Biosensors & Bioelectronics, 6:401-406 (1991).
Shichiri, et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri, et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shults, et al. 1994. A telemetry-instrumentation system for monitoring multiple subcutaneously implanted glucose sensors. IEEE Transactions on Biomedical Engineering 41(10):937-942.
Sokol et al. 1980, Immobilized-enzyme rate-determination method for glucose analysis, Clin. Chem. 26(1):89-92.
Thome et al. 1995. Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thompson, et al., In Vivo Probes: Problems and Perspectives, Department of Chemistry, University of Toronto, Canada, pp. 255-261, 1986.
Tierney et al. 2000. Effect of acetaminophen on the accuracy of glucose measurements obtained with the GlucoWatch biographer. Diabetes Technol Ther 2:199-207.
Turner and Pickup, "Diabetes mellitus: biosensors for research and management," Biosensors, 1:85-115 (1985).
Updike, et al. 1979. Continuous glucose monitor based on an immobilized enzyme electrode detector. J Lab Clin Med, 93(4):518-527.
Updike, et al. 1994 Enzymatic glucose sensor: Improved long-term performance in vitro and in vivo. ASAIO Journal, 40(2):157-163.
Updike, et al. 1997. Principles of long-term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Wagner, et al. 1998. Continuous amperometric monitoring of glucose in a brittle diabetic chimpanzee with a miniature subcutaneous electrode. Proc. Natl. Acad. Sci. A, 95:6379-6382.
Ward, et al. 1999. Assessment of chronically implanted subcutaneous glucose sensors in dogs: The effect of surrounding fluid masses. ASAIO Journal, 45:555-561.
Wilson, et al. 2000. Enzyme-based biosensors for in vivo measurements. Chem. Rev., 100:2693-2704.
Yang et al (1996). "A glucose biosensor based on an oxygen electrode: In-vitro performances in a model buffer solution and in blood plasma," Biomedical Instrumentation & Technology, 30:55-61.
Zhang et al (1993). Electrochemical oxidation of H202 on Pt and Pt + Ir electrodes in physiological buffer and its applicability to H202-based biosensors. J. Electroanal. Chem., 345:253-271.
Zhu et al. (1994). "Fabrication and characterization of glucose sensors based on a microarray H202 electrode." Biosensors & Bioelectronics, 9: 295-300.
Office Action dated Sep. 5, 2006 in U.S. Appl. No. 09/916,711.
Office Action dated Feb. 14, 2006 in U.S. Appl. No. 09/916,711.
Office Action dated Jul. 1, 2005 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Feb. 11, 2004 in U.S. Appl. No. 09/916,711.
Office Action dated Sep. 24, 2003 in U.S. Appl. No. 09/916,711.
Office Action dated Jun. 19, 2008 in U.S. Appl. No. 11/021,162.
Office Action dated Dec. 7, 1998 in U.S. Appl. No. 08/811,473.
Office Action dated Dec. 11, 2008 in U.S. Appl. No. 09/447,227.
Office Action dated Jun. 12, 2008 in U.S. Appl. No. 09/447,227.
Office Action dated Jan. 23, 2008 in U.S. Appl. No. 09/447,227.
Office Action dated Jul. 17, 2007 in U.S. Appl. No. 09/447,227.
Office Action dated Mar. 9, 2007 in U.S. Appl. No. 09/447,227.
Office Action dated Aug. 1, 2006 in U.S. Appl. No. 09/447,227.
Office Action dated Apr. 4, 2006 in U.S. Appl. No. 09/447,227.
Office Action dated Sep. 22, 2005 in U.S. Appl. No. 09/447,227.
Office Action dated Nov. 28, 2003 in U.S. Appl. No. 09/447,227.
Office Action dated Jul. 9, 2003 in U.S. Appl. No. 09/447,227.
Office Action dated Jan. 16, 2003 in U.S. Appl. No. 09/447,227.
Office Action dated Jul. 15, 2002 in U.S. Appl. No. 09/447,227.
Office Action dated Jan. 17, 2002 in U.S. Appl. No. 09/447,227.
Office Action dated Aug. 15, 2001 in U.S. Appl. No. 09/447,227.
Office Action dated Dec. 26, 2007 in U.S. Appl. No. 11/021,046.
Office Action dated Jun. 23, 2008 in U.S. Appl. No. 11/021,046.
Office Action dated Feb. 4, 2009 in U.S. Appl. No. 11/021,046.
Office Action dated Feb. 24, 2006 in U.S. Appl. No. 10/646,333.
Office Action dated Jun. 6, 2005 in U.S. Appl. No. 10/646,333.
Office Action dated Sep. 22, 2004 in U.S. Appl. No. 10/646,333.
Office Action dated Oct. 8, 2008 in U.S. Appl. No. 10/896,637.
Office Action dated Mar. 5, 2009 in U.S. Appl. No. 10/896,637.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated May 11, 2006 in U.S. Appl. No. 10/897,377.
Office Action dated Oct. 18, 2005 in U.S. Appl. No. 10/897,377.
Office Action dated Feb. 9, 2006 in U.S. Appl. No. 10/897,312.
IPRP for PCT/US04/024178 filed Jul. 21, 2004.
ISR and WO for PCT/US04/024178 filed Jul. 21, 2004.
Office Action dated Sep. 12, 2008 in U.S. Appl. No. 10/991,353.
Office Action dated Mar. 4, 2009 in U.S. Appl. No. 10/991,353.
Office Action dated Jan. 27, 2006 in U.S. Appl. No. 11/007,635.
Office Action mailed May 18, 2007 in U.S. Appl. No. 11/543,707.
Office Action dated Dec. 12, 2007 in U.S. Appl. No. 11/543,707.
Office Action dated Jan. 22, 2009 in U.S. Appl. No. 11/692,154.
Office Action mailed May 23, 2007 in U.S. Appl. No. 11/543,539.
Office Action mailed Dec. 12, 2007 in U.S. Appl. No. 11/543,539.
Office Action mailed May 18, 2007 in U.S. Appl. No. 11/543,683.
Office Action mailed Dec. 12, 2007 in U.S. Appl. No. 11/543,683.
Office Action mailed Jun. 5, 2007 in U.S. Appl. No. 11/543,734.
Office Action mailed Dec. 17, 2007 in U.S. Appl. No. 11/543,734.
Office Action dated Jan. 15, 2008 in U.S. Appl. No. 11/034,344.
Office Action dated Nov. 1, 2007 in U.S. Appl. No. 11/034,343.
Office Action dated Jul. 10, 2008 in U.S. Appl. No. 11/034,343.
Office Action dated Dec. 30, 2008 in U.S. Appl. No. 11/034,343.
Office Action dated Sep. 21, 2007 in U.S. Appl. No. 10/838,912.
Office Action dated Mar. 24, 2008 in U.S. Appl. No. 10/838,912.
Office Action dated Jul. 16, 2008 in U.S. Appl. No. 10/838,912.
Office Action mailed Jun. 5, 2008 in U.S. Appl. No. 10/838,909.
Office Action mailed Mar. 16, 2009 in U.S. Appl. No. 10/838,909.
Office Action dated Dec. 24, 2008 in U.S. Appl. No. 10/885,476.
Office Action dated May 17, 2007 in U.S. Appl. No. 11/077,759.
Office Action dated Mar. 31, 2008 in U.S. Appl. No. 11/077,759.
Office Action dated Jul. 10, 2008 in U.S. Appl. No. 11/077,759.
Office Action dated Oct. 31, 2006 in U.S. Appl. No. 11/077,715.
Office Action dated Apr. 10, 2007 in U.S. Appl. No. 11/077,715.

Office Action dated Jul. 26, 2007 in U.S. Appl. No. 11/077,715.
Office Action dated Jan. 28, 2008 in U.S. Appl. No. 11/077,715.
Office Action dated May 12, 2008 in U.S. Appl. No. 11/077,715.
Office Action dated Nov. 12, 2008, 2008 in U.S. Appl. No. 11/077,715.
Office Action dated Oct. 9, 2007 in U.S. Appl. No. 11/077,883.
Office Action dated Jun. 24, 2008 in U.S. Appl. No. 11/077,883.
Office Action dated Sep. 18, 2008 in U.S. Appl. No. 11/077,883.
Office Action dated Apr. 6, 2009 in U.S. Appl. No. 11/077,883.
Office Action dated Sep. 18, 2007 in U.S. Appl. No. 11/078,230.
Office Action dated Jun. 30, 2008 in U.S. Appl. No. 11/078,230.
Office Action dated Sep. 5, 2008 in U.S. Appl. No. 11/078,230.
Office Action dated Jan. 26, 2009 in U.S. Appl. No. 11/078,230.
Office Action dated May 5, 2008 in U.S. Appl. No. 11/078,232.
Office Action dated Nov. 12, 2008 in U.S. Appl. No. 11/078,232.
Office Action dated Mar. 5, 2009 in U.S. Appl. No. 11/078,232.
Office Action dated Jul. 27, 2007 in U.S. Appl. 11/077,714.
Office Action dated Apr. 10, 2007 in U.S. Appl. 11/077,714.
Office Action dated Oct. 11, 2006 in U.S. Appl. 11/077,714.
Office Action dated Jan. 10, 2008 in U.S. Appl. 11/077,714.
Office Action dated Sep. 16, 2008 in U.S. Appl. 11/077,714.
Office Action dated Apr. 16, 2009 in U.S. Appl. 11/077,714.
Office Action dated Jan. 30, 2007 in U.S. Appl. No. 11/077,763.
Office Action dated Apr. 21, 2008 in U.S. Appl. No. 11/077,643.
Office Action dated Oct. 1, 2008 in U.S. Appl. No. 11/077,643.
Office Action dated Mar. 11, 2009 in U.S. Appl. No. 11/077,643.
Office Action dated Sep. 18, 2008 in U.S. Appl. No. 11/439,630.
Office Action dated Feb. 23, 2009 in U.S. Appl. No. 11/439,630.
Office Action dated Jan. 3, 2008 in U.S. Appl. No. 11/157,746.
Office Action dated May 1, 2008 in U.S. Appl. No. 11/157,746.
Office Action dated Jun. 26, 2008 in U.S. Appl. No. 11/157,365.
Office Action dated Jan. 7, 2009 in U.S. Appl. No. 11/157,365.
Office Action dated Jun. 30, 2008 in U.S. Appl. No. 11/360,252.
Office Action dated Jan. 29, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Nov. 28, 2008 in U.S. App. No. 11/333,837.
Office Action dated Nov. 28, 2008 in U.S. App. No. 11/360,250.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Asberg et al. 2003. Hydrogels of a Conducting Conjugated Polymer as 3-D Enzyme Electrode. Biosensors Bioelectronics. pp. 199-207.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Beach et al. 1999. Subminiature implantable potentiostat and modified commercial telemetry device for remote glucose monitoring. IEEE Transactions on Instrumentation and Measurement 48(6):1239-1245.
Bellucci et al. Jan. 1986. Electrochemical behaviour of graphite-epoxy composite materials (GECM) in aqueous salt solutions, Journal of Applied Electrochemistry, 16(1):15-22.
Bessman et al., Progress toward a glucose sensor for the artificial pancreas, Proceedings of a Workshop on Ion-Selective Microelectrodes, Jun. 4-5, 1973, Boston, MA, 189-197.
Bindra et al. 1991. Design and in Vitro Studies of a Needle-Type Glucose Senso for Subcutaneous Monitoring. Anal. Chem 63:1692-96.
Bowman,et al. 1986. The packaging of implantable integrated sensors. IEEE Trans Biomed Eng BME33(2):248-255.
CAI et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Cass et al. "Ferrocene-mediated enzyme electrodes for amperometric determination of glucose," Anal. Chem., 36:667-71 (1984).
Cassidy et al., Apr. 1993. Novel electrochemical device for the detection of cholesterol or glucose, Analyst, 118:415-418.
Chen et al. 2006. A noninterference polypyrrole glucose biosensor. Biosensors and Bioelectronics 22:639-643.
Claremont et al. Jul. 1986. Potentially-implantable, ferrocene-mediated glucose sensor. J. Biomed. Eng. 8:272-274.
Clark et al. 1981. One-minute electrochemical enzymic assay for cholesterol in biological materials, Clin. Chem. 27(12):1978-1982.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Csoregi et al., 1994. Design, characterization, and one-point in vivo calibration of a subcutaneously implanted glucose electrode. Anal Chem. 66(19):3131-3138.
Danielsson et al. 1988. Enzyme thermistors, Methods in Enzymology, 137:181-197.
Davies, et al. 1992. Polymer membranes in clinical sensor applications. I. An overview of membrane function, Biomaterials, 13(14):971-978.
Davis et al. 1983. Bioelectrochemical fuel cell and sensor based on a quinoprotein, alcohol dehydrogenase. *Enzyme Microb. Technol.,* vol. 5, September, 383-388.
Durliat et al. 1976. Spectrophotometric and electrochemical determinations of L(+)-lactate in blood by use of lactate dehydrogenase from yeast, Clin. Chem. 22(11):1802-1805.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Ganesh et al., Evaluation of the VIA® blood chemistry monitor for glucose in healthy and diabetic volunteers, Journal of Diabetese Science and Technology, 2(2):182-193, Mar. 2008.
Heller, A. 1992. Electrical Connection of Enzyme Redox Centers to Electrodes. J. Phys. Chem. 96:3579-3587.
Heller, A. 2003. Plugging metal connectors into enzymes. Nat Biotechnol 21:631-2.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Kacaniklic, May-Jun. 1994. Electroanalysis, 6(5-6):381-390.
Karube et al. 1993. Microbiosensors for acetylcholine and glucose. Biosensors & Bioelectronics 8:219-228.
Kawagoe et al. 1991. Enzyme-modified organic conducting salt microelectrode, Anal. Chem. 63:2961-2965.
Keedy et al. 1991. Determination of urate in undiluted whole blood by enzyme electrode. *Biosensors & Bioelectronics,* 6: 491-499.
Kerner et al. 1988. A potentially implantable enzyme electrode for amperometric measurement of glucose, Horm Metab Res Suppl. 20:8-13.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Maidan et al. 1992. Elimination of Electrooxidizable Interferent-Produced Currents in Amperometric Biosensors, Analytical Chemistry, 64:2889-2896.
Makale et al. 2003. Tissue window chamber system for validation of implanted oxygen sensors. Am. J. Physiol. Heart Circ. Physiol. 284:H2288-2294.
Mascini et al. 1989. Glucose electrochemical probe with extended linearity for whole blood. *J Pharm Biomed Anal* 7(12): 1507-1512.
Matthews et al. 1988. An amperometric needle-type glucose sensor testing in rats and man. Diabetic Medicine 5:248-252.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Mowery et al. 2000. Preparation and characterization of hydrophobic polymeric films that are thromboresistant via nitric oxide release. Biomaterials 21:9-21.
Murphy, et al. 1992. Polymer membranes in clinical sensor applications. II. The design and fabrication of permselective hydrogels for electrochemical devices, Biomaterials, 13(14):979-990.
Myler et al. 2002. Ultra-thin-polysiloxane-film-composite membranes for the optimisation of amperometric oxidase enzyme electrodes. Biosens Bioelectron 17:35-43.
Office Action dated Apr. 11, 2007 in U.S. Appl. No. 10/896,639.
Office Action dated Apr. 12, 2010 in U.S. Appl. No. 11/333,837.
Office Action dated Apr. 27, 2010 in U.S. Appl. No. 11/078,232.
Office Action dated Apr. 6, 2006 in U.S. Appl. No. 10/896,639.
Office Action dated Aug. 22, 2006 in U.S. Appl. No. 10/896,639.
Office Action dated Dec. 3, 2008 in U.S. Appl. No. 11/675,063.
Office Action dated Feb. 10, 2009 in U.S. Appl. No. 11/077,713.
Office Action dated Feb. 19, 2010 in U.S. Appl. No. 11/675,063.
Office Action dated Feb. 23, 2010 in U.S. Appl. No. 12/113,508.
Office Action dated Jan. 20, 2010 in U.S. Appl. No. 11/077,713.
Office Action dated Jan. 22, 2010 in U.S. Appl. No. 11/439,630.
Office Action dated Jun. 10, 2009 in U.S. Appl. No. 11/675,063.
Office Action dated Jun. 24, 2010 in U.S. Appl. No. 12/113,724.
Office Action dated Jun. 29, 2009 in U.S. Appl. No. 11/333,837.
Office Action dated Mar. 11, 2010 in U.S. Appl. No. 11/280,672.
Office Action dated Mar. 14, 2007 in U.S. Appl. No. 10/695,636.
Office Action dated May 5, 2008 in U.S. Appl. No. 11/077,713.
Office Action dated Oct. 29, 2009 in U.S. Appl. No. 11/280,672.
Office Action dated Oct. 5, 2007 in U.S. Appl. No. 10/896,639.
Office Action dated Sep. 2, 2009 in U.S. Appl. No. 11/077,713.
Office Action dated Sep. 2, 2009 in U.S. Appl. No. 11/078,072.
Office Action dated Sep. 23, 2005 in U.S. Appl. No. 10/896,639.
Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Patel et al. 2003. Amperometric glucose sensors based on ferrocene containing polymeric electron transfer systems-a preliminary report. Biosens Bioelectron 18:1073-6.
Pfeiffer, E.F. 1990. The glucose sensor: the missing link in diabetes therapy, Horm Metab Res Suppl. 24:154-164.
Pickup et al. 1988. Progress towards in vivo glucose sensing with a ferrocene-mediated amperometric enzyme electrode. 34-36.
Pickup et al. 1989. Potentially-implantable, amperometric glucose sensors with mediated electron transfer: improving the operating stability. Biosensors 4:109-119.
Pickup et al. 1993. Developing glucose sensors for in vivo use. Elsevier Science Publishers Ltd (UK), TIBTECH vol. 11: 285-291.
Poitout, et al. 1991. In Vitro and In Vivo Evaluation in Dogs of a Miniaturized Glucose Sensor, ASAIO Transactions, 37:M298-M300.
Prabhu et al. 1981. Electrochemical studies of hydrogen peroxide at a platinum disc electrode, Electrochimica Acta 26(6):725-729.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Rebrin et al. 1992. Subcutaenous glucose monitoring by means of electrochemical sensors: fiction or reality? J. Biomed. Eng. 14:33-40.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sansen et al. 1985. "Glucose sensor with telemetry system." in Ko, W. H. (Ed.). Implantable Sensors for Closed Loop Prosthetic Systems. Chap. 12, pp. 167-175, Mount Kisco, NY: Futura Publishing Co.
Schmidt et al. 1993. Glucose concentration in subcutaneous extracellular space. Diabetes Care 16(5):695-700.
Schmidtke et al., Measurement and modeling of the transient difference between blood and subcutaneous glucose concentrations in the rat after injection of insulin. *Proc Natl Aced Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO J, 43:137-142.
Shichiri et al. 1982. Wearable artificial endocrine pancrease with needle-type glucose sensor. Lancet 2:1129-1131.
Stern et al., 1957. Electrochemical polarization: 1. A theoretical analysis of the shape of polarization curves, Journal of the Electrochemical Society, 104(1):56-63.
Sternberg et al. 1988. Covalent enzyme coupling on cellulose acetate membranes for glucose sensor development. Anal. Chem. 69:2781-2786.
Stokes. 1988. Polyether Polyurethanes: Biostable or Not? J. Biomat. Appl. 3:228-259.
Thome-Duret et al. 1996. Use of a subcutaneous glucose sensor to detect decreases in glucose concentration prior to observation in blood, Anal. Chem. 68:3822-3826.
Torjman et al., Glucose monitoring in acute care: technologies on the horizon, Journal of Deabetes Science and Technology, 2(2):178-181, Mar. 2008.
Tse et al. 1987. Time-Dependent Inactivation of Immobilized Glucose Oxidase and Catalase. Biotechnol. Bioeng. 29:705-713.
TURNERet al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Turner, A.P.F. 1988. Amperometric biosensor based on mediator-modified electrodes. Methods in Enzymology 137:90-103.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 2000. A subcutaneous glucose sensor with improved longevity, dynamic range, and stability of calibration. Diabetes Care 23(2):208-214.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Velho et al. 1989. Strategies for calibrating a subcutaneous glucose sensor. Biomed Biochim Acta 48(11/12):957-964.
Wang et al. 1994. Highly Selective Membrane-Free, Mediator-Free Glucose Biosensor. Anal. Chem. 66:3600-3603.

Wilkins et al. 1988. The coated wire electrode glucose sensor, Horm Metab Res Suppl., 20:50-55.
Wilkins et al. 1995. Integrated implantable device for long-term glucose monitoring. Biosens. Bioelectron 10:485-494.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)- modified myoglobin, Electrochemistry Communications 1 (1999) 603-611.
Yamasakiet al. 1989. Direct measurement of whole blood glucose by a needle-type sensor. Clinica Chimica Acta. 93:93-98.
Yamasaki, Yoshimitsu. Sep. 1984. The development of a needle-type glucose sensor for wearable artificial endocrine pancreas. Medical Journal of Osaka University 35(1-2):25-34.
Yanget al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal Of Membrane Science 237:145-161.
Zamzow et al. 1990. Development and evaluation of a wearable blood glucose monitor, ASAIO Transactions; 36(3): pp. M588-M591.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.
Zhu et al. 2002. Planar amperometric glucose sensor based on glucose oxidase immobilized by chitosan film on prussian blue layer. Sensors, 2:127-136.
Abel, P. U.; von Woedtke, T. Biosensors for in vivo glucose measurement: can we cross the experimental stage. Biosens Bioelectron 2002, 17, 1059-1070.
Baker et al. 1993. Dynamic concentration challenges for biosensor characterization. *Biosensors & Bioelectronics,* 8:433-441.
Bindra et al. 1989. Pulsed amperometric detection of glucose in biological fluids at a surface-modified gold electrode. *Anal Chem,* 61:2566-2570.
Bisenberger et al. 1995. A triple-step potential waveform at enzyme multisensors with thick-film gold electrodes for detection of glucose and sucrose. *Sensors and Actuators,* B 28:181-189.
Bott, A. W. 1997. A comparison of cyclic voltammetry and cyclic staircase voltammetry. *Current Separations,* 16(1):23-26.
Bott, A. 1998. Electrochemical methods for the determination of glucose. *Current Separations,* 17(1)25-31.
Choleau et al. 2002. Calibration of a subcutaneo amperometric glucose sensor. Part 1. Effect of measurement uncertainties on the determination of sensor sensitivity and background current. *Biosensors and Bioelectronics,* 17:641-646.
Dixon et al. 2002. Characterization in vitro and in vivo of the oxygen dependence of an enzyme/polymer biosensor for monitoring brain glucose. *Journal of Neuroscience Methods,* 119:135-142.
Gilligan et al. Feasibility of continuous long-term glucose monitoring from a subcutaneous glucose sensor in humans. Diabetes Technol. Ther. 2004, 6, 378-386.
Hall et al. 1998. Electrochemical oxidation of hydrogen peroxide at platinum electrodes. Part 1. An adsorption-controlled mechanism. *Electrochimica Acta,* 43(5-6):579-588.
Hall et al. 1998. Electrochemical oxidation of hydrogen peroxide at platinum electrodes. Part II: Effect of potential. *Electrochimica Acta;* 43(14-15):2015-2024.
Hall et al. 1999. Electrochemical oxidation of hydrogen peroxide at platinum electrodes. Part III: Effect of temperature. *Electrochimica Acta,* 44:2455-2462.
Hall et al. 1999. Electrochemical oxidation of hydrogen peroxide at platinum electrodes. Part IV: Phosphate buffer dependence. *Electrochimica Acta,* 44:4573-4582.
Hall et al. 2000. Electrochemical oxidation of hydrogen peroxide at platinum electrodes. Part V: Inhibition by chloride. *Electrochimica Acta,* 45:3573-3579.
Heller, A. Implanted electrochemical glucose sensors for the management of diabetes. Annu Rev Biomed Eng 1999, 1, 153-175.
Hitchman, M. L. 1978. "Measurement of Dissolved Oxygen." In Elving et al. (Eds.). Chemical Analysis, vol. 49, Chap. 3, pp. 34-49, 59-123. New York: John Wiley & Sons.
Huang et al. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.
Jablecki et al. 2000. Simulations of the frequency response of Implantable glucose sensors. *Analytical Chemistry,* 72:1853-1859.
Jaremko et al. 1998. Advances toward the implantable artificial pancreas for treatment of diabetes. *Diabetes Care,* 21(3):444-450.
Jensen et al. 1997. Fast wave forms for pulsed electrochemical detection of glucose by incorporation of reductive desorption of oxidation products. *Analytical Chemistry,* 69(9):1776-1781.
Kang et al. In vitro and short-term in vivo characteristics of a Kel-F thin film modified glucose sensor. Anal Sci 2003, 19, 1481-1486.
Kraver et al. A mixed-signal sensor interface microinstrument. Sensors and Actuators A: Physical 2001, 91, 266-277.
LaCourse et al. 1993. Optimization of waveforms for pulsed amperometric detection of carbohydrates based on pulsed voltammetry. *Analytical Chemistry,* 65:50-52.
Lerner et al. 1984. An implantable electrochemical glucose sensor. *Ann. N. Y. Acad. Sci.,* 428:263-278.
Leypoldt et al. 1984. Model of a two-substrate enzyme electrode for glucose. *Anal. Chem.,* 56:2896-2904.
McGrath et al. The use of differential measurements with a glucose biosensor for interference compensation during glucose determinations by flow injection analysis. Biosens Bioelectron 1995, 10, 937-943.
Memoli et al. A comparison between different immobilised glucoseoxidase-based electrodes. J Pharm Biomed Anal 2002, 29, 1045-1052.
Neuburger et al. 1987. Pulsed amperometric detection of carbohydrates at gold electrodes with a two-step potential waveform. *Anal. Chem.,* 59:150-154.
Postlethwaite et al. 1996. Interdigitated array electrode as an alternative to the rotated ring-disk electrode for determination of the reaction products of dioxygen reduction. *Analytical Chemistry,* 68:2951-2958.
Rhodes et al. 1994. Prediction of pocket-portable and implantable glucose enzyme electrode performance from combined species permeability and digital simulation analysis. *Analytical Chemistry,* 66(9):1520-1529.
Sansen et al. 1990. A smart sensor for the voltammetric measurement of oxygen or glucose concentrations. *Sensors and Actuators, B* 1:298-302.
Wang et al. Improved ruggedness for membrane-based amperometric sensors using a pulsed amperometric method. Anal Chem 1997, 69, 4482-4489.
Ward et al. Understanding Spontaneous Output Fluctuations of an Amperometric Glucose Sensor: Effect of Inhalation Anesthesia and e of a Nonenzyme Containing Electrode. ASAIO Journal 2000, 540-546.
Ward et al. 2000. Rise in background current over time in a subcutaneous glucose sensor in the rabbit: Relevance to calibration and accuracy. *Biosensors & Bioelectronics,* 15:53-61.
Ward et al. 2002. A new amperometric glucose microsensor: In vitro and short-term in vivo evaluation. *Biosensors & Bioelectronics,* 17:181-189.
Wientjes, K. J. C. Development of a glucose sensor for diabetic patients. 2000.
Wilkins et al. Glucose monitoring: state of the art and future possibilities. Med Eng Phys 1995, 18, 273-288.
Wilson et al. 1992. Progress toward the development of an implantable sensor for glucose. *Clin. Chem.,* 38(9):1613-1617.
Wu et al. 1999. In situ electrochemical oxygen generation with an immunoisolation device. *Ann. N.Y. Acad. Sci.,* 875:105-125.
Zhang et al. 1994. Elimination of the acetaminophen interference in an implantable glucose sensor. Analytical Chemistry, 66(7):1183-1188.
U.S. Appl. No. 09/447,227, filed Nov. 22, 2999.
U.S. Appl. No. 10/838,658, filed May 3, 2004.

U.S. Appl. No. 10/838,909, filed May 3, 2004.
U.S. Appl. No. 10/838,912, filed May 3, 2004.
U.S. Appl. No. 10/885,476, filed Jul. 6, 2004.
U.S. Appl. No. 10/897,377, filed Jul. 21, 2004.
Bott, A.W. 1997. A Comparison of cyclic voltammetry and staircase voltammetry. Current Separations, 16(1):23-26.*
Wilson, et al. 1992. Progress toward the development of an implantable sensor for glucose. Clin. Chem., 38(9):1613-1617.*
Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol. Ther. 2004, 6, 378-386.
Kang, S. K.; Jeong, R.A.; Park, S.; Chung, T. D.; Park, S.; Kim, H.C. In vitro and short-term in vivo characteristics of a Kel-F thin film modified glucose sensor. Anal Sci 2003, 19, 1481-1486.
Kraver, K.; Gutha, M. R.; Strong, T.; Bird, P.; Cha, G.; Hoeld, W., Brown, R. A mixed-signal sensor interface microinstrument. Sensors and Actuators A: Physical 2001, 91, 266-277.
McGrath, M. J.; Iwuoha, E. I.; Diamond, D.; Smyth, M. R. The use of differential measurements with a glucose biosensor for interference compensation during glucose determinations by flow injection analysis. Biosens Bioelectron 1995, 10, 937-943.
Rhodes, et al. 1994 Prediction of pocket-portable and implantable glucose enzyme electrode performance from combined species permeability and digital simulation analysis. *Analytical Chemistry,* 66(9):1520-1529.
Sansen, et al. 1990. A smart sensor for the voltammetric measurement of oxygen or glucose concentrations. *Sensors and Actuators,* B 1:298-302.
Wang, X.; Pardue, H. L. Improved ruggedness for membrane-based amperometric sensors using a pulsed amperometric method. Anal Chem 1997, 69, 4482-4489.
Ward, W. K.; Wood, M. D.; Troupe, J. E. Understanding Spontaneous Output Fluctuations of an Amperometric Glucose Sensor: Effect of Inhalation Anesthesia and e of a Nonenzyme Containing Electrode. ASAIO Journal 2000, 540-546.
Ward, et al. 2000. Rise in background current over time in a subcutaneous glucose sensor in the rabbit: Relevance to calibration and accuracy. *Biosensors & Bioelectronics,* 15:53-61.
Ward, et al. 2002. A new amperometric glucose microsensor: In vitro and short-term in vivo evaluation, *Biosensors & Bioelectronics,* 17:181-189.
Wilkins, et al. 1995. Integrated implantable device for long-term glucose monitoring. *Biosens. Bioelectron.,* 10:485-494.

* cited by examiner

ELECTRODE SYSTEMS FOR ELECTROCHEMICAL SENSORS

Matter enclosed in heavy brackets [ ] appears in the original patent but forms no part of this reissue specification; matter printed in italics indicates the additions made by reissue.

RELATED APPLICATION

This application claims the benefit of priority under 35 U.S.C. § 119(e) to U.S. Provisional Application No. 60/490,007, filed Jul. 25, 2003, the contents of which are hereby incorporated by reference in their entirety.

FIELD OF THE INVENTION

The present invention relates generally to systems and methods for improving electrochemical sensor performance.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are spread apart so far that the diabetic will likely find out too late, sometimes incurring dangerous side effects, of a hyperglycemic or hypoglycemic condition. It is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuously detecting and/or quantifying blood glucose values. Many implantable glucose sensors suffer from complications within the body and provide only short-term or less-than-accurate working of blood glucose. Similarly, transdermal sensors have problems in accurately working and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have occurred.

SUMMARY OF THE PREFERRED EMBODIMENTS

In contrast to the prior art, the sensors of preferred embodiments advantageously generate oxygen to allow the sensor to function at sufficient oxygen levels independent of the oxygen concentration in the surrounding environment. In another aspect of the preferred embodiments, systems and methods for modifying electrochemical interferants are provided.

Accordingly, in a first embodiment, an electrochemical sensor for determining a presence or a concentration of an analyte in a fluid is provided, the sensor comprising a membrane system comprising an enzyme, wherein the enzyme reacts with the analyte; an electroactive surface comprising a working electrode, the working electrode comprising a conductive material and configured to measure a product of the reaction of the enzyme with the analyte; and an auxiliary electrode comprising a conductive material and configured to generate oxygen, wherein the auxiliary electrode is situated such that the oxygen generated diffuses to the enzyme or to the electroactive surface.

In an aspect of the first embodiment, the auxiliary electrode comprises a conductive material selected from the group consisting of a conductive metal, a conductive polymer, and a blend of a conductive metal and a conductive polymer.

In an aspect of the first embodiment, the auxiliary electrode comprises a form selected from the group consisting of a mesh, a grid, and a plurality of spaced wires.

In an aspect of the first embodiment, the auxiliary electrode comprises a polymer, wherein the polymer is situated on a surface of the auxiliary electrode.

In an aspect of the first embodiment, the polymer comprises a material that is impermeable to glucose but is permeable to oxygen.

In an aspect of the first embodiment, the polymer comprises a material that is impermeable to glucose but is permeable to oxygen and permeable to interfering species.

In an aspect of the first embodiment, the polymer comprises a material having a molecular weight that blocks glucose and allows transport therethrough of oxygen, urate, ascorbate, and acetaminophen.

In an aspect of the first embodiment, the polymer comprises a material that is permeable to glucose and oxygen.

In an aspect of the first embodiment, the polymer comprises a material that is permeable to glucose, oxygen, and interfering species.

In an aspect of the first embodiment, the polymer comprises a material having a molecular weight that allows transport therethrough of oxygen, glucose, urate, ascorbate, and acetaminophen.

In an aspect of the first embodiment, the auxiliary electrode is configured to be set at a potential of at least about +0.6 V.

In an aspect of the first embodiment, the auxiliary electrode is configured to electrochemically modify an electrochemical interferant to render the electrochemical interferent substantially electrochemically non-reactive at the working electrode.

In an aspect of the first embodiment, the auxiliary electrode is configured to be set at a potential of at least about +0.1 V.

In a second embodiment, an electrochemical sensor for determining a presence or a concentration of an analyte in a fluid is provided, the sensor comprising a membrane system comprising an enzyme, wherein the enzyme reacts with the analyte; an electroactive surface comprising a working electrode, the working electrode comprising a conductive material and configured to measure a product of the reaction of the enzyme with the analyte; and an auxiliary electrode comprising a conductive material and configured to modify an electrochemical interferant such that the electrochemical interferent is rendered substantially electrochemically non-reactive at the working electrode.

In an aspect of the second embodiment, the auxiliary electrode comprises a conductive material selected from the group consisting of a conductive metal, a conductive polymer, and a blend of a conductive metal and a conductive polymer.

In an aspect of the second embodiment, the auxiliary electrode comprises a form selected from the group consisting of a mesh, a grid, and a plurality of spaced wires.

In an aspect of the second embodiment, the auxiliary electrode comprises a polymer, wherein the polymer is situated on a surface of the auxiliary electrode.

In an aspect of the second embodiment, the polymer comprises a material that is permeable to an electrochemical interferant.

In an aspect of the second embodiment, the polymer comprises a material that is impermeable to glucose but is permeable to oxygen.

In an aspect of the second embodiment, the polymer comprises a material that is impermeable to glucose but is permeable to oxygen and interferants.

In an aspect of the second embodiment, the polymer comprises a material having a molecular weight that blocks glucose and allows transport therethrough of oxygen, urate, ascorbate, and acetaminophen.

In an aspect of the second embodiment, the polymer comprises a material that is permeable to glucose and oxygen.

In an aspect of the second embodiment, the polymer comprises a material that is permeable to glucose, oxygen, and interferants.

In an aspect of the second embodiment, the polymer comprises a material having a molecular weight that allows transport therethrough of oxygen, glucose, urate, ascorbate, and acetaminophen.

In an aspect of the second embodiment, the auxiliary electrode is configured to be set at a potential of at least about +0.1V.

In an aspect of the second embodiment, the auxiliary electrode is configured to generate oxygen.

In an aspect of the second embodiment, the auxiliary electrode is configured to be set at a potential of at least about +0.6 V.

In a third embodiment, an electrochemical sensor is provided comprising an electroactive surface configured to measure an analyte; and an auxiliary interferant-modifying electrode configured to modify an electrochemical interferant such that the electrochemical interferant is rendered substantially non-reactive at the electroactive surface.

In an aspect of the third embodiment, the auxiliary interferant-modifying electrode comprises a conductive material selected from the group consisting of a conductive metal, a conductive polymer, and a blend of a conductive metal and a conductive polymer.

In an aspect of the third embodiment, the auxiliary interferant-modifying electrode comprises a form selected from the group consisting of a mesh, a grid, and a plurality of spaced wires.

In an aspect of the third embodiment, the auxiliary interferant-modifying electrode comprises a polymer, wherein the polymer is situated on a surface of the auxiliary interferant-modifying electrode.

DETAILED DESCRIPTION OF THE PREFERRED EMBODIMENT

Figure 1:
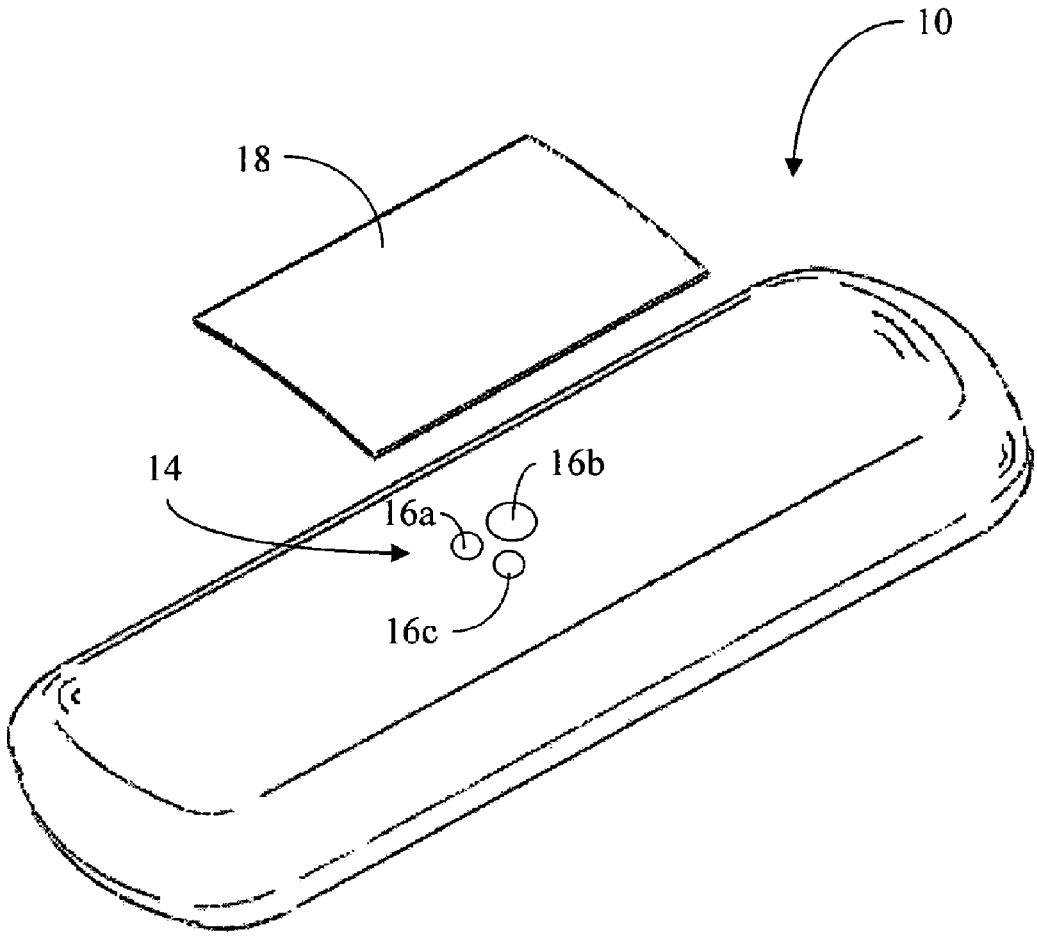
FIG. 1 is an exploded perspective view of one exemplary embodiment of a implantable glucose sensor.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms and are used in their ordinary sense, including, without limitation, one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The term "signal output," as used herein, is a broad term and is used in its ordinary sense, including, without limitation, an analog or digital signal directly related to the measured analyte from the analyte-measuring device. The term broadly encompasses a single point, or alternatively, a plurality of time spaced data points from a substantially continuous glucose sensor, which comprises individual measurements taken at time intervals ranging from fractions of a second up to, for example, 1, 2, or 5 minutes or longer.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "potentiostat," as used herein, is a broad term and is used in its ordinary sense, including, without limitation, an electrical system that controls the potential between the working and reference electrodes of a three-electrode cell at a preset value independent of resistance changes between the electrodes. It forces whatever current is necessary to flow between the working and counter electrodes to keep the desired potential, as long as the cell voltage and current do not exceed the compliance limits of the potentiostat.

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. The sensing region generally comprises a non-conductive body, a working electrode, a reference electrode, and optionally a counter electrode passing through and secured within the body forming electrochemically reactive surfaces on the body and an electronic connective means at another location on the body, and a multi-domain membrane system affixed to the body and covering the electrochemically reactive surface.

The terms "raw data stream" and "data stream," as used herein, are broad terms and are used in their ordinary sense, including, without limitation, an analog or digital signal directly related to the measured an analyte from an analyte sensor. In one example, the raw data stream is digital data in "counts" converted by an A/D converter from an analog signal (for example, voltage or amps) representative of a analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The terms "electrical potential" and "potential" as used herein, are broad terms and are used in their ordinary sense, including, without limitation, the electrical potential difference between two points in a circuit which is the cause of the flow of a current.

The term "ischemia," as used herein, is a broad term and is used in its ordinary sense, including, without limitation, local and temporary deficiency of blood supply due to obstruction of circulation to a part (for example, a sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts that have a higher amplitude than system noise," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and characterized by a higher amplitude than system noise.

The term "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The phrase "distal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

The preferred embodiments relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples.

The sensor uses any known method, including invasive, minimally invasive, and non-invasive sensing techniques, to provide an output signal indicative of the concentration of the analyte of interest. The sensor is of the type that senses a product or reactant of an enzymatic reaction between an analyte and an enzyme in the presence of oxygen as a measure of the analyte in vivo or in vitro. Such a sensor typically comprises a membrane surrounding the enzyme through which a bodily fluid passes and in which an analyte within the bodily fluid reacts with an enzyme in the presence of oxygen to generate a product. The product is then measured using electrochemical methods and thus the output of an electrode system functions as a measure of the analyte. In some embodiments, the sensor can use an amperometric, coulometric, conductimetric, and/or potentiometric technique for measuring the analyte. In some embodiments, the electrode system can be used with any of a variety of known in vitro or in vivo analyte sensors or monitors.

FIG. 1 is an exploded perspective view of one exemplary embodiment of an implantable glucose sensor 10 that utilizes an electrode system 16. In this exemplary embodiment, a body with a sensing region 14 includes an electrode system (16a to 16c), also referred to as the electroactive sensing surface, and sensor electronics, which are described in more detail with reference to FIG. 2.

In this embodiment, the electrode system 16 is operably connected to the sensor electronics (FIG. 2) and includes electroactive surfaces (including two-, three- or more electrode systems), which are covered by a membrane system 18. The membrane system 18 is disposed over the electroactive surfaces of the electrode system 16 and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (interference domain); and/or 5) hydrophilicity at the electrochemically reactive surfaces of the sensor interface (electrolyte domain), for example, such as described in co-pending U.S. patent application Ser. No. 10/838,912, filed May 3, 2004 and entitled "IMPLANTABLE ANALYTE SENSOR," the contents of which are incorporated herein by reference in their entirety. The membrane system can be attached to the sensor body by mechanical or chemical methods such as described in co-pending U.S. patent application Ser. No. 10/885,476, filed Jul. 6, 2004 and entitled, "SYSTEMS AND METHODS FOR MANUFACTURE OF AN ANALYTE-MEASURING DEVICE INCLUDING A MEMBRANE SYSTEM" and U.S. patent application Ser. No. 10/838,912 filed May 3, 2004 and entitled, "IMPLANTABLE ANALYTE SENSOR", which are incorporated herein by reference in their entirety.

In the embodiment of FIG. 1, the electrode system 16 includes three electrodes (working electrode 16a, counter electrode 16b, and reference electrode 16c), wherein the counter electrode is provided to balance the current generated by the species being measured at the working electrode. In the case of a glucose oxidase based glucose sensor, the species measured at the working electrode is $H_2O_2$. Glucose oxidase, GOX, catalyzes the conversion of oxygen and glucose to hydrogen peroxide and gluconate according to the following reaction:

$$\text{GOX}+\text{Glucose}+O_2 \rightarrow \text{Gluconate}+H_2O_2+\text{reduced GOX}$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2H+), two electrons (2e−), and one oxygen molecule ($O_2$). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is further consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In some embodiments, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, one limitation of prior art enzymatic-based electrochemical analyte sensors can be caused by oxygen deficiencies, which is described in more detail with reference to FIG. 3.

Figure 2:
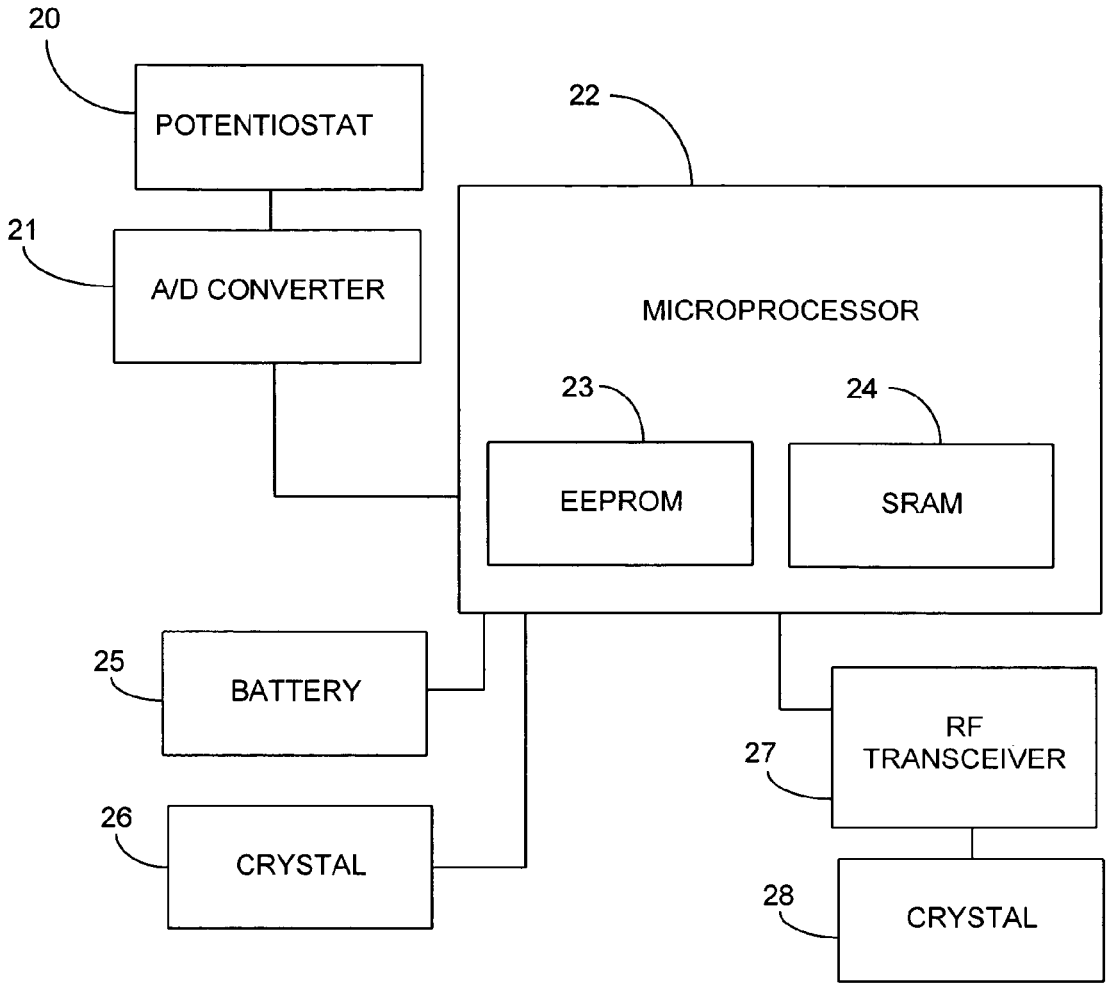
FIG. 2 is a block diagram that illustrates sensor electronics in one exemplary embodiment.

FIG. 2 is a block diagram that illustrates sensor electronics in one exemplary embodiment; one skilled in the art appreciates however that a variety of sensor electronics configurations can be implemented with the preferred embodiments. In this embodiment, a potentiostat 20 is shown, which is operatively connected to electrode system 16 (FIG. 1) to obtain a current value, and includes a resistor (not shown) that translates the current into voltage. The A/D converter 21 digitizes the analog signal into "counts" for processing. Accordingly, the resulting raw data signal in counts is directly related to the current measured by the potentiostat.

A microprocessor 22 is the central control unit that houses EEPROM 23 and SRAM 24, and controls the processing of the sensor electronics. The alternative embodiments can utilize a computer system other than a microprocessor to process data as described herein. In some alternative embodiments, an application-specific integrated circuit (ASIC) can be used for some or all the sensor's central processing. EEPROM 23 provides semi-permanent storage of data, storing data such as sensor ID and necessary programming to process data signals (for example, programming for data smoothing such as described elsewhere herein). SRAM 24 is used for the system's cache memory, for example for temporarily storing recent sensor data.

The battery 25 is operatively connected to the microprocessor 22 and provides the necessary power for the sensor. In one embodiment, the battery is a Lithium Manganese Dioxide battery, however any appropriately sized and powered battery can be used. In some embodiments, a plurality of batteries can be used to power the system. Quartz crystal 26 is operatively connected to the microprocessor 22 and maintains system time for the computer system.

The RF Transceiver 27 is operably connected to the microprocessor 22 and transmits the sensor data from the sensor to a receiver. Although a RF transceiver is shown here, some other embodiments can include a wired rather than wireless connection to the receiver. In yet other embodiments, the sensor can be transcutaneously connected via an inductive coupling, for example. The quartz crystal 28 provides the system time for synchronizing the data transmissions from the RF transceiver. The transceiver 27 can be substituted with a transmitter in one embodiment.

Although FIGS. 1 and 2 and associated text illustrate and describe an exemplary embodiment of an implantable glucose sensor, the electrode systems of the preferred embodiments described below can be implemented with any known electrochemical sensor, including U.S. Pat. No. 6,001,067 to Shults et al.; U.S. Pat. No. 6,702,857 to Brauker et al.; U.S. Pat. No. 6,212,416 to Ward et al.; U.S. Pat. No. 6,119,028 to Schulman et al; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al; to U.S. Pat. No. 5,985,129 to Gough et al.; WO Patent Application Publication No. 2004/021877 to Caduff; U.S. Pat. No. 5,494,562 to Maley et al.; U.S. Pat. No. 6,120,676 to Heller et al.; and U.S. Pat. No. 6,542,765 to Guy et al., co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA," the contents of each of which are incorporated herein by reference in their entirety.

Figure 3:
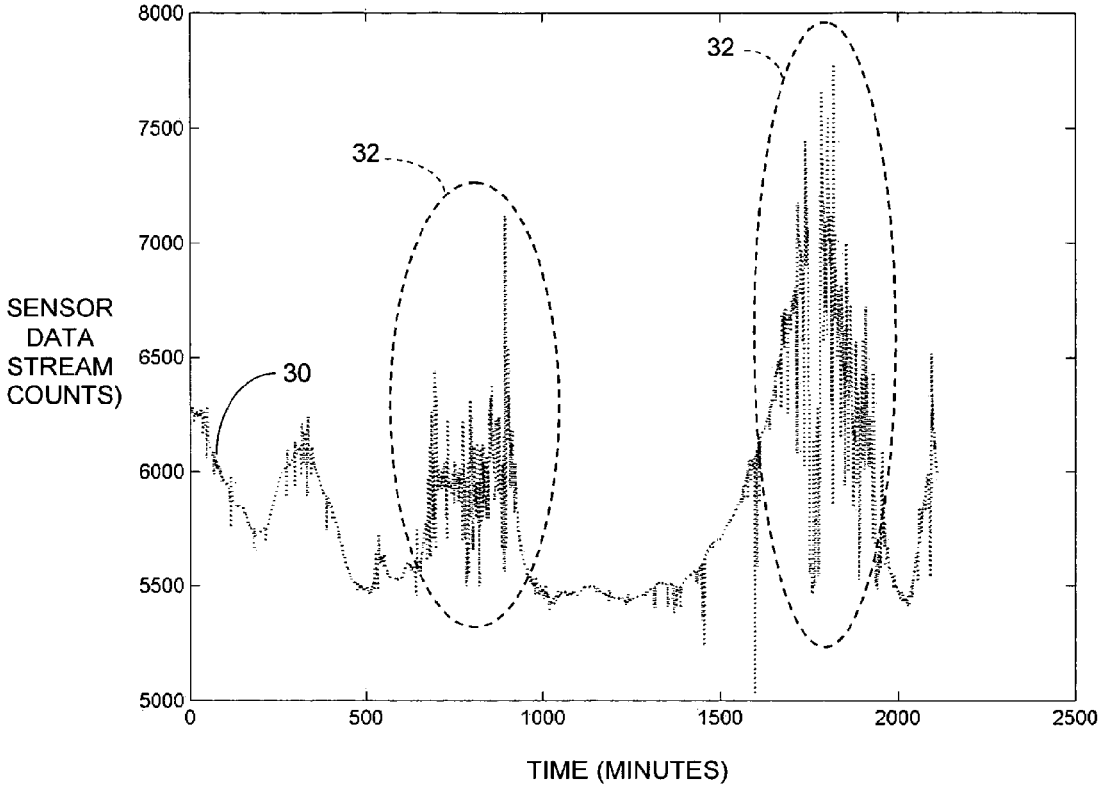
FIG. 3 is a graph that shows a raw data stream obtained from a glucose sensor without an auxiliary electrode of the preferred embodiments.

FIG. 3 is a graph that depicts a raw data stream obtained from a prior art glucose sensor such as described with reference to FIG. 1. The x-axis represents time in minutes. The y-axis represents sensor data in counts. In this example, sensor output in counts is transmitted every 30-seconds. The raw data stream 30 includes substantially smooth sensor output in some portions, however other portions exhibit erroneous or transient non-glucose related signal artifacts 32. Particularly, referring to the signal artifacts 32, it is believed that effects of local ischemia on prior art electrochemical sensors creates erroneous (non-glucose) signal values due to oxygen deficiencies either at the enzyme within the membrane system and/or at the counter electrode on the electrode surface.

In one situation, when oxygen is deficient relative to the amount of glucose, then the enzymatic reaction is limited by oxygen rather than glucose. Thus, the output signal is indicative of the oxygen concentration rather than the glucose concentration, producing erroneous signals. Additionally, when an enzymatic reaction is rate-limited by oxygen, glucose is expected to build up in the membrane because it is not completely catabolized during the oxygen deficit. When oxygen is again in excess, there is also excess glucose due to the transient oxygen deficit. The enzyme rate then speeds up for a short period until the excess glucose is catabolized, resulting in spikes of non-glucose related increased sensor output. Accordingly, because excess oxygen (relative to glucose) is necessary for proper sensor function, transient ischemia can result in a loss of signal gain in the sensor data.

In another situation, oxygen deficiency can be seen at the counter electrode when insufficient oxygen is available for reduction, which thereby affects the counter electrode in that it is unable to balance the current coming from the working electrode. When insufficient oxygen is available for the counter electrode, the counter electrode can be driven in its electrochemical search for electrons all the way to its most negative value, which could be ground or 0.0 V, which causes the reference to shift, reducing the bias voltage, such is as described in more detail below. In other words, a common result of ischemia a drop off in sensor current as a function of glucose concentration (for example, lower sensitivity). This happens because the working electrode no longer oxidizes all of the $H_2O_2$ arriving at its surface because of the reduced bias. In some extreme circumstances, an increase in glucose can produce no increase in current or even a decrease in current.

In some situations, transient ischemia can occur at high glucose levels, wherein oxygen can become limiting to the enzymatic reaction, resulting in a non-glucose dependent downward trend in the data. In some situations, certain movements or postures taken by the patient can cause transient signal artifacts as blood is squeezed out of the capillaries resulting in local ischemia and causing non-glucose dependent signal artifacts. In some situations, oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue. However, such ischemic periods can cause an oxygen deficit in implanted devices that can last for many minutes or even an hour or longer.

Although some examples of the effects of transient ischemia on a prior art glucose sensor are described above, similar effects can be seen with analyte sensors that use alternative catalysts to detect other analytes, for example, amino acids (amino acid oxidase), alcohol (alcohol oxidase), galactose (galactose oxidase), lactate (lactate oxidase), cholesterol (cholesterol oxidase), or the like.

Another problem with conventional electrochemical sensors is that they can electrochemically react not only with the analyte to be measured (or by-product of the enzymatic reaction with the analyte), but additionally can react with other electroactive species that are not intentionally being measured (for example, interfering species), which causes an increase in signal strength due to these "interfering species". In other words, interfering species are compounds with an oxidation or reduction potential that overlaps with the analyte to be measured (or the by-product of the enzymatic reaction with the analyte). For example, in a conventional amperometric glucose oxidase-based glucose sensor wherein the sensor measures hydrogen peroxide, interfering species such as acetaminophen, ascorbate, and urate are known to produce inaccurate signal strength when they are not properly controlled.

Some conventional glucose sensors utilize a membrane system that blocks at least some interfering species, such as ascorbate and urate. In some such systems, at least one layer of the membrane system includes a porous structure that has a relatively impermeable matrix with a plurality of "micro holes" or pores of molecular dimensions, such that transfer through these materials is primarily due to passage of species through the pores (for example, the layer acts as a microporous barrier or sieve blocking interfering species of a particular size). In other such systems, at least one layer of the membrane system defines a permeability that allows selective dissolution and diffusion of species as solutes through the layer. Unfortunately, it is difficult to find membranes that are satisfactory or reliable in use, especially in vivo, which effectively block all interferants and/or interfering species in some embodiments.

Electrochemical Sensors of the Preferred Embodiments

In one aspect of the preferred embodiments, an electrochemical sensor is provided with an auxiliary electrode configured to generate oxygen in order to overcome the effects of transient ischemia. In another aspect of the preferred embodiments, an electrochemical sensor is provided with an auxiliary electrode configured to electrochemically modify (for example, oxidize or reduce) electrochemical interferants to render them substantially non-electroactively reactive at the electroactive sensing surface(s) in order to overcome the effects of interferants on the working electrode.

It is known that oxygen can be generated as a product of electrochemical reactions occurring at a positively charged electrode (for example, set at about +0.6 to about +1.2 V or more). One example of an oxygen producing reaction is the electrolysis of water, which creates oxygen at the anode (for example, the working electrode). In the exemplary electrochemical glucose sensor, glucose is converted to hydrogen peroxide by reacting with glucose oxidase and oxygen, after which the hydrogen peroxide is oxidized at the working electrode and oxygen is generated therefrom. It is noted that one challenge to generating oxygen electrochemically in this way is that while an auxiliary electrode does produce excess oxygen, the placement of the auxiliary electrode in proximity to the analyte-measuring working electrode can cause oxidation of hydrogen peroxide at the auxiliary electrode, resulting in reduced signals at the working electrode. It is also known that many electrochemical interferants can be reduced at a potential of from about +0.1V to +1.2V or more; for example, acetaminophen is reduced at a potential of about +0.4 V.

Accordingly, the sensors of preferred embodiments place an auxiliary electrode above the electrode system 16, or other electroactive sensing surface, thereby reducing or eliminating the problem of inaccurate signals as described above.

Figure 4:
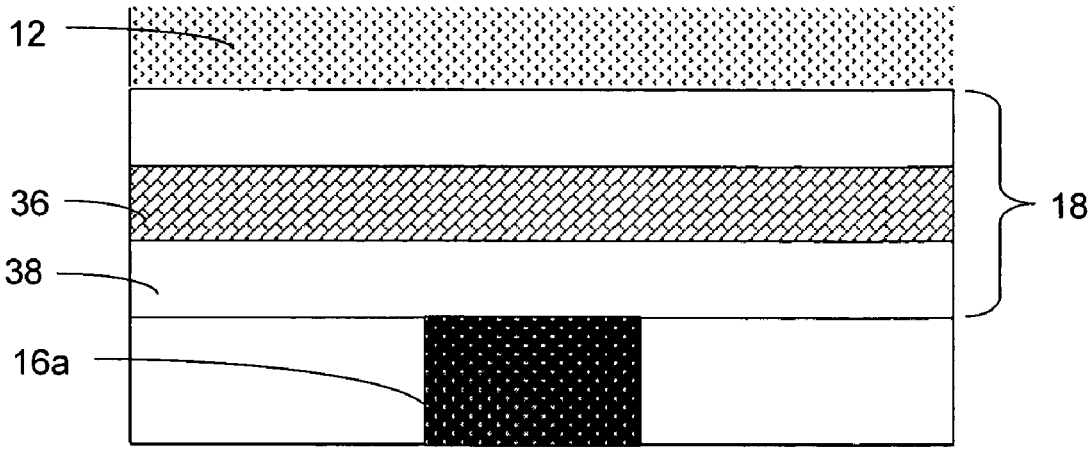
FIG. 4 is a side schematic illustration of a portion of an electrochemical sensor of the preferred embodiments, showing an auxiliary electrode placed proximal to the enzyme domain within a membrane system.

FIG. 4 is a side schematic illustration of a portion of the sensing region of an electrochemical sensor of the preferred embodiments, showing an auxiliary electrode between the enzyme and the outside solution while the working (sensing) electrode is located below the enzyme and further from the outside solution. Particularly, FIG. 4 shows an external solution 12, which represents the bodily or other fluid to which the sensor is exposed in vivo or in vitro.

The membrane system 18 includes a plurality of domains (for example, cell impermeable domain, resistance domain, enzyme domain, and/or other domains such as are described in U.S. Published Patent Application 2003/0032874 to Rhodes et al. and copending U.S. patent application Ser. No. 10/885,476, filed Jul. 6, 2004 and entitled, "SYSTEMS AND METHODS FOR MANUFACTURE OF AN ANALYTE-MEASURING DEVICE INCLUDING A MEMBRANE SYSTEM", the contents of which are incorporated herein by reference in their entireties) is located proximal to the external solution and finctions to transport fluids necessary for the enzymatic reaction, while protecting inner components of the sensor from harsh biohazards, for example. Although each domain is not independently shown, the enzyme 38 is shown disposed between an auxiliary electrode 36 and the working electrode 16a in the illustrated embodiment.

Preferably, the auxiliary electrode 36 is located within or adjacent to the membrane system 18, for example, between the enzyme and other domains, although the auxiliary electrode can be placed anywhere between the electroactive sensing surface and the outside fluid. The auxiliary electrode 36 is formed from known working electrode materials (for example, platinum, palladium, graphite, gold, carbon, conductive polymer, or the like) and has a voltage setting that produces oxygen (for example, from about +0.6 V to +1.2 V or more) and/or that electrochemically modifies (for example, reduces) electrochemical interferants to render them substantially non-reactive at the electroactive sensing surface(s) (for example, from about +0.1 V to +1.2 V or more). The auxiliary electrode can be a mesh, grid, plurality of spaced wires or conductive polymers, or other configurations designed to allow analytes to penetrate therethrough.

In the aspect of the preferred embodiments wherein the auxiliary electrode 36 is configured to generate oxygen, the oxygen generated from the auxiliary electrode 36 diffuses upward and/or downward to be utilized by the enzyme 38 and/or the counter electrode (depending on the placement of the auxiliary electrode). Additionally, the analyte (for example, glucose) from the outside solution (diffuses through the auxiliary electrode 36) reacts with the enzyme 38 and produces a measurable product (for example, hydrogen peroxide). Therefore, the product of the enzymatic reaction diffuses down to the working electrode 16a for accurate measurement without being eliminated by the auxiliary electrode 36.

In one alternative embodiment, the auxiliary electrode 36 can be coated with a polymeric material, which is impermeable to glucose but permeable to oxygen. By this coating, glucose will not electroactively react at the auxiliary electrode 36, which can otherwise cause at least some of the glucose to pre-oxidize as it passes through the auxiliary electrode 36 (when placed above the enzyme), which can prevent accurate glucose concentration measurements at the working electrode in some sensor configurations. In one embodiment, the polymer coating comprises silicone, however any polymer that is selectively permeable to oxygen, but not glucose, can be used. The auxiliary electrode 16 can be coated by any known process, such as dip coating or spray coating, after which is can be blown, blotted, or the like to maintain spaces within the electrode for glucose transport.

In another alternative embodiment, the auxiliary electrode 36 can be coated with a polymeric material that is permeable to glucose and oxygen and can be placed between the enzyme and the outside fluid. Consequently, the polymeric coating will cause glucose from the outside fluid to electroactively react at the auxiliary electrode 36, thereby limiting the amount of glucose that passes into the enzyme 38, and thus reducing the amount of oxygen necessary to successfully react with all available glucose in the enzyme. The polymeric material can function in place of or in combination with the resistance domain in order to limit the amount of glucose that passes through the membrane system. This embodiment assumes a stoichiometric relationship between glucose oxidation and decreased sensor signal output, which can be compensated for by calibration in some sensor configurations. Additionally, the auxiliary electrode generates oxygen, further reducing the likelihood of oxygen becoming a rate-limiting factor in the enzymatic reaction and/or at the counter electrode, for example.

In another aspect of the preferred embodiments, the auxiliary electrode 36 is configured to electrochemically modify (for example, oxidize or reduce) electrochemical interferants to render them substantially non-reactive at the electroactive sensing surface(s). In these embodiments, which can be in addition to or alternative to the above-described oxygen-generating embodiments, a polymer coating is chosen to selectively allow interferants (for example, urate, ascorbate, and/or acetaminophen such as described in U.S. Pat. No. 6,579,690 to Bonnecaze, et al.) to pass through the coating and electrochemically react with the auxiliary electrode, which effectively pre-oxidizes the interferants, rendering them substantially non-reactive at the working electrode 16a. In one exemplary embodiment, silicone materials can be synthesized to allow the transport of oxygen, acetaminophen and other interferants, but not allow the transport of glucose. In some embodiments, the polymer coating material can be chosen with a molecular weight that blocks glucose and allows the transport of oxygen, urate, ascorbate, and acetaminophen. In another exemplary embodiment, silicone materials can be synthesized to allow the transport of oxygen, glucose, acetaminophen, and other interferants. In some embodiments, the polymer coating material is chosen with a molecular weight that allows the transport of oxygen, glucose, urate, ascorbate, and acetaminophen. The voltage setting necessary to react with interfering species depends on the target electrochemical interferants, for example, from about +0.1 V to about +1.2 V. In some embodiments, wherein the auxiliary electrode is set at a potential of from about +0.6 to about +1.2 V, both oxygen-generation and electrochemical interferant modification can be achieved. In some embodiments, wherein the auxiliary electrode is set at a potential below about +0.6 V, the auxiliary electrode will function mainly to electrochemically modify interferants, for example.

Therefore, the sensors of preferred embodiments reduce or eliminate oxygen deficiency problems within electrochemical sensors by producing oxygen at an auxiliary electrode located above the enzyme within an enzyme-based electrochemical sensor. Additionally or alternatively, the sensors of preferred embodiments reduce or eliminate interfering species problems by electrochemically reacting with interferants at the auxiliary electrode rendering them substantially non-reactive at the working electrode.

Methods and devices that are suitable for use in conjunction with aspects of the preferred embodiments are disclosed in co-pending U.S. patent application Ser. No. 10/842,716, filed May 10, 2004 and entitled, "MEMBRANE SYSTEMS INCORPORATING BIOACTIVE AGENTS"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR MEMBRANE SYSTEM"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. application Ser. No. 60/489,615 filed Jul. 23, 2003 and entitled "ROLLED ELECTRODE ARRAY AND ITS METHOD FOR MANUFACTURE"; U.S. application Ser. No. 60/490,010 filed Jul. 25, 2003 and entitled "INCREASING BIAS FOR OXYGEN PRODUCTION IN AN ELECTRODE ASSEMBLY"; U.S. application Ser. No. 60/490,009 filed Jul. 25, 2003 and entitled "OXYGEN ENHANCING ENZYME MEMBRANE FOR ELECTROCHEMICAL SENSORS"; U.S. application Ser. No. 60/490,007 filed Jul. 25, 2003 and entitled "OXYGEN-GENERATING ELECTRODE FOR USE IN ELECTROCHEMICAL SENSORS"; U.S. application Ser. No. 10/896,637 filed Jul. 21, 2004 and entitled "ROLLED ELECTRODE ARRAY AND ITS METHOD FOR MANUFACTURE"; U.S. application Ser. No. 10/896,772 filed Jul. 21, 2004 and entitled "INCREASING BIAS FOR OXYGEN PRODUCTION IN AN ELECTRODE SYSTEM"; U.S. application Ser. No. 10/896,639 filed Jul. 21, 2004 and entitled "OXYGEN ENHANCING MEMBRANE SYSTEMS FOR IMPLANTABLE DEVICES"; U.S. application Ser. No. 10/897,377 filed Jul. 21, 2004 and entitled "ELECTROCHEMICAL SENSORS INCLUDING ELECTRODE SYSTEMS WITH INCREASED OXYGEN GENERATION". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An electrochemical sensor for determining a presence or a concentration of an analyte in a fluid, the sensor comprising:

a membrane system comprising an enzyme, wherein the enzyme reacts with the analyte;

an electroactive surface comprising a working electrode, the working electrode comprising a conductive material and configured to measure a product of the reaction of the enzyme with the analyte; and an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is situated on a surface of the auxiliary electrode, and wherein the polymer comprises a material that is directly impermeable to glucose but is permeable to oxygen.

2. The electrochemical sensor of claim 1, wherein the auxiliary electrode comprises a conductive material selected from the group consisting of a conductive metal, a conductive polymer, and a blend of a conductive metal and a conductive polymer.

3. The electrochemical sensor of claim 1, wherein the auxiliary electrode comprises a form selected from the group consisting of a mesh, a grid, and a plurality of spaced wires.

4. The electrochemical sensor of claim 1, wherein the polymer comprises a material that is permeable to interfering species.

5. The electrochemical sensor of claim 4, wherein the polymer comprises a material having a molecular weight that allows transport therethrough of oxygen, urate, ascorbate, and acetaminophen.

6. The electrochemical sensor of claim 1, wherein the auxiliary electrode is configured to be set at a potential of at least about +0.6 V.

7. The electrochemical sensor of claim 1, wherein the auxiliary electrode is configured to electrochemically modify an electrochemical [interferant] *interferent* to render the electrochemical interferent substantially electrochemically non-reactive at the working electrode.

8. The electrochemical sensor of claim 7, wherein the auxiliary electrode is configured to be set at a potential of at least about +0.1 V.

9. The electrochemical sensor of claim 1, configured for measuring a concentration of glucose in a fluid.

10. The electrochemical sensor of claim 1, configured for insertion into a subcutaneous tissue of a host.

11. The electrochemical sensor of claim 1, configured for implantation into a subcutaneous tissue of a host.

12. The electrochemical sensor of claim 1, configured for measuring a concentration of glucose substantially without an oxygen deficit.

13. An electrochemical sensor for determining a presence or a concentration of an analyte in a fluid, the sensor comprising:

a membrane system comprising an enzyme, wherein the enzyme reacts with the analyte;

an electroactive surface comprising a working electrode, the working electrode comprising a conductive material and configured to measure a product of the reaction of the enzyme with the analyte; and an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is directly situated on a surface of the auxiliary electrode, and wherein the polymer comprises a material that is impermeable to glucose but is permeable to oxygen and permeable to interfering species.

14. The electrochemical sensor of claim 13, wherein the polymer comprises a material having a molecular weight that blocks glucose and allows transport therethrough of oxygen, urate, ascorbate, and acetaminophen.

15. The electrochemical sensor of claim 13, wherein the auxiliary electrode comprises a conductive material selected from the group consisting of a conductive metal, a conductive polymer, and a blend of a conductive metal and a conductive polymer.

16. The electrochemical sensor of claim 13, wherein the auxiliary electrode comprises a form selected from the group consisting of a mesh, a grid, and a plurality of spaced wires.

17. The electrochemical sensor of claim 13, wherein the polymer comprises a material having a molecular weight that allows transport therethrough of urate, ascorbate, and acetaminophen.

18. The electrochemical sensor of claim 13, wherein the auxiliary electrode is configured to be set at a potential of at least about +0.6 V.

19. The electrochemical sensor of claim 13, wherein the auxiliary electrode is configured to electrochemically modify an electrochemical [interferant] *interferent* to render the electrochemical interferent substantially electrochemically non-reactive at the working electrode.

20. The electrochemical sensor of claim 19, wherein the auxiliary electrode is configured to be set at a potential of at least about +0.1 V.

21. The electrochemical sensor of claim 13, configured for measuring a concentration of glucose in a fluid.

22. The electrochemical sensor of claim 13, configured for insertion into a subcutaneous tissue of a host.

23. The electrochemical sensor of claim 13, configured for implantation into a subcutaneous tissue of a host.

24. The electrochemical sensor of claim 13, configured for measuring a concentration of glucose substantially without an oxygen deficit.

25. An electrochemical sensor for determining a presence or a concentration of an analyte in a fluid, the sensor comprising:

a membrane system comprising an enzyme, wherein the enzyme reacts with the analyte;

an electroactive surface comprising a working electrode, the working electrode comprising a conductive material and configured to measure a product of the reaction of the enzyme with the analyte; and an auxiliary electrode comprising a conductive material and configured to modify an electrochemical [interferant] *interferent* such that the electrochemical interferent is rendered substantially electrochemically non-reactive at the working electrode, wherein the auxiliary electrode comprises a polymer, wherein the polymer is situated on a surface of the auxiliary electrode, and wherein the polymer comprises a material that is impermeable to glucose but is permeable to oxygen.

26. The electrochemical sensor of claim 25, wherein the auxiliary electrode comprises a conductive material selected from the group consisting of a conductive metal, a conductive polymer, and a blend of a conductive metal and a conductive polymer.

27. The electrochemical sensor of claim 25, wherein the auxiliary electrode comprises a form selected from the group consisting of a mesh, a grid, and a plurality of spaced wires.

28. The electrochemical sensor of claim 25, wherein the polymer comprises a material that is permeable to an electrochemical [interferant] *interferent*.

29. The electrochemical sensor of claim 25, wherein the polymer comprises a material that is impermeable to glucose but is permeable to oxygen and [interferants] *interferents*.

30. The electrochemical sensor of claim 25, wherein the auxiliary electrode is configured to be set at a potential of at least about +0.1V.

31. The electrochemical sensor of claim 25, wherein the auxiliary electrode is configured to generate oxygen.

32. The electrochemical sensor of claim 31, wherein the auxiliary electrode is configured to be set at a potential of at least about +0.6 V.

33. The electrochemical sensor of claim 25, configured for measuring a concentration of glucose in a fluid.

34. The electrochemical sensor of claim 25, configured for insertion into a subcutaneous tissue of a host.

35. The electrochemical sensor of claim 25, configured for implantation into a subcutaneous tissue of a host.

36. The electrochemical sensor of claim 25, configured for measuring a concentration of glucose substantially without an oxygen deficit.

37. The electrochemical sensor of claim 25, wherein the auxiliary electrode is configured to generate oxygen.

38. The electrochemical sensor of claim 37, wherein the auxiliary electrode is configured to be set at a potential of at least about +0.6 V.

39. An electrochemical sensor for determining a presence or a concentration of an analyte in a fluid, the sensor comprising:

a membrane system comprising an enzyme, wherein the enzyme reacts with the analyte;

an electroactive surface comprising a working electrode, the working electrode comprising a conductive material and configured to measure a product of the reaction of the enzyme with the analyte; and an auxiliary electrode comprising a conductive material and configured to modify an electrochemical [interferant] *interferent* such that the electrochemical interferent is rendered substantially electrochemically non-reactive at the working electrode, wherein the auxiliary electrode comprises a polymer, wherein the polymer is situated on a surface of the auxiliary electrode, and wherein the polymer comprises a material having a molecular weight that blocks glucose and allows transport therethrough of oxygen, urate, ascorbate, and acetaminophen.

40. The electrochemical sensor of claim 39, wherein the auxiliary electrode comprises a conductive material selected from the group consisting of a conductive metal, a conductive polymer, and a blend of a conductive metal and a conductive polymer.

41. The electrochemical sensor of claim 39, wherein the auxiliary electrode comprises a form selected from the group consisting of a mesh, a grid, and a plurality of spaced wires.

42. The electrochemical sensor of claim 39, wherein the polymer comprises a material that is permeable to an electrochemical [interferant] *interferent*.

43. The electrochemical sensor of claim 39, wherein the polymer comprises a material that is permeable to [interferants] *interferents*.

44. The electrochemical sensor of claim 39, wherein the auxiliary electrode is configured to be set at a potential of at least about +0.1V.

45. The electrochemical sensor of claim 39, wherein the auxiliary electrode is configured to generate oxygen.

46. The electrochemical sensor of claim 45, wherein the auxiliary electrode is configured to be set at a potential of at least about +0.6 V.

47. The electrochemical sensor of claim 39, configured for measuring a concentration of glucose in a fluid.

48. The electrochemical sensor of claim 39, configured for insertion into a subcutaneous tissue of a host.

49. The electrochemical sensor of claim 39, configured for implantation into a subcutaneous tissue of a host.

50. The electrochemical sensor of claim 39, configured for measuring a concentration of glucose substantially without an oxygen deficit.

*51. An electrochemical sensor for measuring a concentration of an analyte in a biological fluid, the sensor comprising:*

*a membrane system comprising an enzyme configured to react with the analyte;*

*an electroactive surface comprising a working electrode, the working electrode comprising a conductive material and configured to measure a product of the reaction of the enzyme with the analyte; and*

*an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is situated on a surface of the auxiliary electrode, and wherein the polymer comprises a material that is permeable or impermeable to glucose but is permeable to oxygen, and wherein the sensor is configured such that the auxiliary electrode is located between the electroactive surface of the working electrode and the biological fluid being measured.*

*52. The electrochemical sensor of claim 51, wherein the auxiliary electrode comprises a conductive material selected from the group consisting of a conductive metal, a conductive polymer, and a blend of a conductive metal and a conductive polymer.*

*53. The electrochemical sensor of claim 51, wherein the auxiliary electrode comprises a form selected from the group consisting of a mesh, a grid, and a plurality of spaced wires.*

*54. The electrochemical sensor of claim 51, wherein the polymer comprises a material having a molecular weight that allows transport therethrough of oxygen, urate, ascorbate, and acetaminophen.*

*55. The electrochemical sensor of claim 51, wherein the auxiliary electrode is configured to be set at a potential of at least about +0.6 V.*

*56. The electrochemical sensor of claim 51, wherein the auxiliary electrode is configured to electrochemically modify an electrochemical interferent to render the electrochemical interferent substantially electrochemically non-reactive at the working electrode.*

*57. The electrochemical sensor of claim 56, wherein the auxiliary electrode is configured to be set at a potential of at least about +0.1 V.*

*58. The electrochemical sensor of claim 51, configured for measuring a concentration of glucose in a fluid.*

*59. The electrochemical sensor of claim 51, configured for measuring a concentration of glucose substantially without an oxygen deficit.*

*60. An electrochemical sensor for measuring a concentration of an analyte in a biological fluid, the sensor comprising:*

*a membrane system comprising an enzyme configured to react with the analyte;*

*an electroactive surface comprising a working electrode, the working electrode comprising a conductive material and configured to measure a product of the reaction of the enzyme with the analyte; and*

*an auxiliary electrode comprising a conductive material and configured to generate oxygen, wherein the auxiliary electrode is situated at a location directly between the electroactive surface and the biological fluid being measured such that the oxygen generated diffuses to the enzyme or to the electroactive surface, wherein the auxiliary electrode comprises a polymer, wherein the polymer is directly situated on a surface of the auxiliary electrode, and wherein the polymer comprises a material that is permeable or impermeable to glucose but is permeable to oxygen and permeable to one or more interfering species.*

*61. The electrochemical sensor of claim 60, wherein the polymer comprises a material having a molecular weight that blocks glucose and allows transport therethrough of oxygen, urate, ascorbate, and acetaminophen.*

*62. The electrochemical sensor of claim 60, wherein the auxiliary electrode comprises a conductive material selected from the group consisting of a conductive metal, a conductive polymer, and a blend of a conductive metal and a conductive polymer.*

*63. The electrochemical sensor of claim 60, wherein the auxiliary electrode comprises a form selected from the group consisting of a mesh, a grid, and a plurality of spaced wires.*

*64. The electrochemical sensor of claim 60, wherein the polymer comprises a material having a molecular weight that allows transport therethrough of urate, ascorbate, and acetaminophen.*

*65. The electrochemical sensor of claim 60, wherein the auxiliary electrode is configured to be set at a potential of at least about +0.6 V.*

*66. The electrochemical sensor of claim 60, wherein the auxiliary electrode is configured to electrochemically modify an electrochemical interferent to render the electrochemical interferent substantially electrochemically non-reactive at the working electrode.*

*67. The electrochemical sensor of claim 66, wherein the auxiliary electrode is configured to be set at a potential of at least about +0.1 V.*

*68. The electrochemical sensor of claim 60, configured for measuring a concentration of glucose in a fluid.*

*69. The electrochemical sensor of claim 60, configured for insertion into a subcutaneous tissue of a host.*

*70. The electrochemical sensor of claim 60, configured for implantation into a subcutaneous tissue of a host.*

*71. The electrochemical sensor of claim 60, configured for measuring a concentration of glucose substantially without an oxygen deficit.*

*72. An electrochemical sensor for determining a presence or a concentration of an analyte in a fluid, the sensor comprising:*

*a membrane system comprising an enzyme configured to react with the analyte;*

*an electroactive surface comprising a working electrode, the working electrode comprising a conductive material and configured to measure a product of the reaction of the enzyme with the analyte; and*

*an auxiliary electrode comprising a conductive material and configured to modify an electrochemical interferent such that the electrochemical interferent is rendered substantially electrochemically non-reactive at the working electrode, wherein the auxiliary electrode comprises a polymer, wherein the polymer is situated on a surface of the auxiliary electrode such that at least a portion of the polymer is located more distal to the electroactive surface than the auxiliary electrode, and wherein the polymer comprises a material that is permeable or impermeable to glucose but is permeable to oxygen.*

*73. The electrochemical sensor of claim 72, wherein the auxiliary electrode comprises a conductive material selected from the group consisting of a conductive metal, a conductive polymer, and a blend of a conductive metal and a conductive polymer.*

*74. The electrochemical sensor of claim 72, wherein the auxiliary electrode comprises a form selected from the group consisting of a mesh, a grid, and a plurality of spaced wires.*

*75. The electrochemical sensor of claim 72, wherein the polymer comprises a material that is permeable to an electrochemical interferent.*

*76. The electrochemical sensor of claim 72, wherein the polymer comprises a material that is impermeable to glucose but is permeable to oxygen and interferents.*

*77. The electrochemical sensor of claim 72, wherein the auxiliary electrode is configured to be set at a potential of at least about +0.1 V.*

*78. The electrochemical sensor of claim 72, wherein the auxiliary electrode is configured to generate oxygen.*

*79. The electrochemical sensor of claim 78, wherein the auxiliary electrode is configured to be set at a potential of at least about +0.6 V.*

*80. The electrochemical sensor of claim 72, configured for measuring a concentration of glucose in a fluid.*

*81. The electrochemical sensor of claim 72, configured for insertion into a subcutaneous tissue of a host.*

*82. The electrochemical sensor of claim 72, configured for implantation into a subcutaneous tissue of a host.*

*83. The electrochemical sensor of claim 72, configured for measuring a concentration of glucose substantially without an oxygen deficit.*

*84. The electrochemical sensor of claim 72, wherein the auxiliary electrode is configured to generate oxygen.*

*85. The electrochemical sensor of claim 84, wherein the auxiliary electrode is configured to be set at a potential of at least about +0.6 V.*

*86. An electrochemical sensor for determining a presence or a concentration of an analyte in a fluid, the sensor comprising:*

*a membrane system comprising an enzyme configured to react with the analyte;*

*an electroactive surface comprising a working electrode, the working electrode comprising a conductive material and configured to measure a product of the reaction of the enzyme with the analyte; and*

*an auxiliary electrode comprising a conductive material and configured to modify an electrochemical interferent such that the electrochemical interferent is rendered substantially electrochemically non-reactive at the working electrode, wherein the auxiliary electrode located within or adjacent to a membrane system such that at least a portion of the membrane system is located more distal to the electroactive surface than the auxiliary electrode, and wherein the membrane system comprises a polymer comprising a material having a molecular weight that allows transport therethrough of oxygen, urate, ascorbate, and acetaminophen.*

*87. The electrochemical sensor of claim 86, wherein the auxiliary electrode comprises a conductive material selected from the group consisting of a conductive metal, a conductive polymer, and a blend of a conductive metal and a conductive polymer.*

*88. The electrochemical sensor of claim 86, wherein the auxiliary electrode comprises a form selected from the group consisting of a mesh, a grid, and a plurality of spaced wires.*

*89. The electrochemical sensor of claim 86, wherein the polymer comprises a material that is permeable to an electrochemical interferent.*

*90. The electrochemical sensor of claim 86, wherein the polymer comprises a material that is permeable to interferents.*

*91. The electrochemical sensor of claim 86, wherein the auxiliary electrode is configured to be set at a potential of at least about +0.1 V.*

*92. The electrochemical sensor of claim 86, wherein the auxiliary electrode is configured to generate oxygen.*

*93. The electrochemical sensor of claim 92, wherein the auxiliary electrode is configured to be set at a potential of at least about +0.6 V.*

*94. The electrochemical sensor of claim 86, configured for measuring a concentration of glucose in a fluid.*

*95. The electrochemical sensor of claim 86, configured for insertion into a subcutaneous tissue of a host.*

*96. The electrochemical sensor of claim 86, configured for implantation into a subcutaneous tissue of a host.*

*97. The electrochemical sensor of claim 86, configured for measuring a concentration of glucose substantially without an oxygen deficit.*

*98. An electrochemical sensor for measuring a concentration of an analyte in a biological fluid in a host, the sensor comprising:*

*a membrane system comprising: a cell impermeable domain configured to contact a biological fluid in a host and an enzyme domain comprising enzyme, wherein the enzyme reacts with the analyte;*

*a working electrode comprising a conductive material and configured to measure a product of the reaction of the enzyme with the analyte; and*

*an auxiliary electrode located within or adjacent to the membrane system and comprising a conductive material and configured to modify an electrochemical interferent such that the electrochemical interferent is rendered substantially electrochemically non-reactive at the working electrode.*

*99. The sensor of claim 98, configured for measuring a concentration of glucose in a host.*

*100. The sensor of claim 98, configured for insertion into contact with a subcutaneous tissue of a host.*

*101. The sensor of claim 98, configured for communication with the intravascular system of a host.*

*102. The sensor of claim 98, configured for continuous measurement of the analyte in a host.*

*103. The sensor of claim 98, further comprising a potentiostat operably connected to the working electrode.*

*104. The sensor of claim 103, wherein the potentiostat enables continuous measurement of the analyte in a host.*

*105. The sensor of claim 98, further comprising sensor electronics operably connected to the working electrode, wherein the sensor electronics are configured to transmit data to a receiver.*

*106. The sensor of claim 105, wherein the sensor electronics comprise an RF transceiver configured to wirelessly transmit the data to a receiver.*

*107. The sensor of claim 98, wherein the membrane system is configured to limit diffusion of the analyte there through.*

*108. The sensor of claim 107, wherein the membrane system further comprises a resistance domain configured to limit diffusion of the analyte there through.*

*109. The sensor of claim 98, wherein the membrane system is configured to limit or block one or more interfering species there through.*

*110. The sensor of claim 109, wherein the membrane system further comprises an interference domain configured to limit or block the one or more interfering species there through.*

*111. The sensor of claim 109, wherein the membrane system further comprises an electrolyte domain configured to provide the hydrophilicity at the working electrode.*

*112. The sensor of claim 98, wherein the membrane system is configured to provide a hydrophilicity at the working electrode.*

*113. The sensor of claim 98, wherein the cell impermeable domain is located more distal from the working electrode than any other domain of the membrane system such that the cell impermeable domain directly contacts the host when placed into contact with the host's dermis, subcutaneous tissue and/or intravascular system.*

*114. The sensor of claim 98, wherein the auxiliary electrode is located within the cell impermeable domain.*

*115. The sensor of claim 98, wherein the auxiliary electrode is located between the cell impermeable domain and the enzyme domain.*

*116. An electrochemical sensor for continuous measurement of a concentration of an analyte in an in vivo biological environment, the sensor comprising:*

*a membrane comprising an outermost layer configured for protection of the sensor from the biological environment, wherein the membrane further comprises an enzyme configured to react with the analyte;*

*a working electrode comprising a conductive material and configured to measure a product of the reaction of the enzyme with the analyte; and*

*an auxiliary electrode located within or adjacent to the membrane and comprising a conductive material, wherein the auxiliary electrode is configured to modify an electrochemical interferent such that the electrochemical interferent is rendered substantially electrochemically non-reactive at the working electrode.*

*117. The sensor of claim 116, configured for measuring a concentration of glucose in a host.*

*118. The sensor of claim 116, configured for insertion into contact with a subcutaneous tissue of a host.*

*119. The sensor of claim 116, configured for communication with the intravascular system of a host.*

*120. The sensor of claim 116, further comprising a potentiostat operably connected to the working electrode.*

*121. The sensor of claim 120, wherein the potentiostat enables continuous measurement of the analyte in a host.*

*122. The sensor of claim 116, further comprising sensor electronics operably connected to the working electrode, wherein the sensor electronics are configured to transmit data to a receiver.*

*123. The sensor of claim 122, wherein the sensor electronics comprise an RF transceiver configured to wirelessly transmit the data to a receiver.*

*124. The sensor of claim 116, wherein the membrane is configured to limit diffusion of the analyte there through.*

*125. The sensor of claim 124, wherein the membrane further comprises a resistance domain configured to limit diffusion of the analyte there through.*

*126. The sensor of claim 116, wherein the membrane is configured to limit or block one or more interfering species there through.*

*127. The sensor of claim 126, wherein the membrane further comprises an interference domain configured to limit or block the one or more interfering species there through.*

*128. The sensor of claim 116, wherein the membrane is configured to provide a hydrophilicity at the working electrode.*

*129. The sensor of claim 128, wherein the membrane further comprises an electrolyte domain configured to provide the hydrophilicity at the working electrode.*

*130. The sensor of claim 116, wherein the cell impermeable domain is located more distal from the working electrode than any other domain of the membrane such that the cell impermeable domain directly contacts the host when placed into contact with the host's dermis, subcutaneous tissue and/or intravascular system.*

*131. The sensor of claim 116, wherein the auxiliary electrode is located within the outermost layer.*

*132. The sensor of claim 116, wherein the auxiliary electrode is located between the outermost layer and the enzyme.*

*133. An electrochemical sensor for measuring a concentration of an analyte in a biological fluid, the sensor comprising:*

*a membrane system comprising an enzyme configured to react with an analyte;*

*an electroactive surface comprising a working electrode, the working electrode comprising a conductive material and configured to measure a product of a reaction of the enzyme with the analyte; and*

*an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is situated on a surface of the auxiliary electrode, wherein the polymer comprises a material that is permeable or impermeable to glucose but is permeable to oxygen, and wherein the sensor is configured such that the auxiliary electrode is located between the electroactive surface of the working electrode and a biological fluid in which a concentration of the analyte is being measured;*

*wherein the sensor is configured for insertion or implantation into a subcutaneous tissue of a host.*

*134. The electrochemical sensor of claim 133, wherein the auxiliary electrode comprises a conductive material selected from the group consisting of a conductive metal, a conductive polymer, and a blend of a conductive metal and a conductive polymer.*

*135. The electrochemical sensor of claim 133, wherein the auxiliary electrode comprises a form selected from the group consisting of a mesh, a grid, and a plurality of spaced wires.*

*136. The electrochemical sensor of claim 133, wherein the polymer comprises a material that is permeable to interfering species.*

*137. The electrochemical sensor of claim 136, wherein the polymer comprises a material having a molecular weight that allows transport therethrough of oxygen, urate, ascorbate, and acetaminophen.*

*138. The electrochemical sensor of claim 133, wherein the auxiliary electrode is configured to be set at a potential of at least about +0.6 V.*

*139. The electrochemical sensor of claim 133, wherein the auxiliary electrode is configured to electrochemically modify an electrochemical interferent to render the electrochemical interferent substantially electrochemically non-reactive at the working electrode.*

*140. The electrochemical sensor of claim 139, wherein the auxiliary electrode is configured to be set at a potential of at least about +0.1 V.*

*141. The electrochemical sensor of claim 133, configured for measuring a concentration of glucose in a fluid.*

*142. The electrochemical sensor of claim 133, configured for measuring a concentration of glucose substantially without an oxygen deficit.*

*143. An electrochemical sensor for measuring a concentration of an analyte in a biological fluid, the sensor comprising:*

*a membrane system comprising an enzyme configured to react with an analyte;*

*an electroactive surface comprising a working electrode, the working electrode comprising a conductive material and configured to measure a product of a reaction of the enzyme with the analyte; and*

*an auxiliary electrode comprising a conductive material and configured to generate oxygen, wherein the auxiliary electrode is situated such that the oxygen generated diffuses to the enzyme or to the electroactive surface, wherein the auxiliary electrode comprises a polymer, wherein the polymer is situated on a surface of the auxiliary electrode, wherein the polymer comprises a material that is permeable or impermeable to glucose but is permeable to oxygen, wherein the polymer comprises a material that is permeable to interfering species, and wherein the sensor is configured such that the auxiliary electrode is located between the electroactive surface of the working electrode and a biological fluid in which a concentration of the analyte is being measured.*

*144. The electrochemical sensor of claim 143, wherein the auxiliary electrode comprises a conductive material selected from the group consisting of a conductive metal, a conductive polymer, and a blend of a conductive metal and a conductive polymer.*

*145. The electrochemical sensor of claim 143, wherein the auxiliary electrode comprises a form selected from the group consisting of a mesh, a grid, and a plurality of spaced wires.*

*146. The electrochemical sensor of claim 143, wherein the polymer comprises a material that is permeable to interfering species.*

*147. The electrochemical sensor of claim 146, wherein the polymer comprises a material having a molecular weight that allows transport therethrough of oxygen, urate, ascorbate, and acetaminophen.*

*148. The electrochemical sensor of claim 143, wherein the auxiliary electrode is configured to be set at a potential of at least about +0.6 V.*

*149. The electrochemical sensor of claim 143, wherein the auxiliary electrode is configured to electrochemically modify an electrochemical interferent to render the electrochemical interferent substantially electrochemically non-reactive at the working electrode.*

*150. The electrochemical sensor of claim 149, wherein the auxiliary electrode is configured to be set at a potential of at least about +0.1 V.*

*151. The electrochemical sensor of claim 143, configured for measuring a concentration of glucose in a fluid.*

*152. The electrochemical sensor of claim 143, configured for measuring a concentration of glucose substantially without an oxygen deficit.*

* * * * *

UNITED STATES PATENT AND TRADEMARK OFFICE

CERTIFICATE OF CORRECTION

PATENT NO. : RE43,399 E
APPLICATION NO. : 12/139305
DATED : May 22, 2012
INVENTOR(S) : Simpson et al.

It is certified that error appears in the above-identified patent and that said Letters Patent is hereby corrected as shown below:

| Issued Patent Column | Line | Description of Discrepancy |
|---|---|---|
| (Item 56) Title Page 5 Col. 2 | 6 | Under Other Publications, change "hypoglycaemic" to --hypoglycemic--. |
| (Item 56) Title Page 5 Col. 2 | 26 | Under Other Publications, change "reliablity" to --reliability--. |
| (Item 56) Title Page 5 Col. 2 | 31 | Under Other Publications, change "Hypoglycaemia-" to --Hypoglycemia- --. |
| (Item 56) Title Page 6 Col. 1 | 57 | Under Other Publications, change "impleated" to --implanted--. |
| (Item 56) Title Page 7 Col. 1 | 4 | Under Other Publications, after "Nov. 12, 2008," delete "2008". |
| (Item 56) Title Page 7 Col. 1 | 64 | Under Other Publications, change "Senso" to --Sensor--. |
| (Item 56) Title Page 7 Col. 1 | 66 | Under Other Publications, change "Bowman,et" to --Bowman et--. |
| (Item 56) Title Page 7 Col. 2 | 38 | Under Other Publications, change "Diabetese" to --Diabetes--. |
| (Item 56) Title Page 8 Col. 1 | 2 | Under Other Publications, change "Electronanalysis" to --Electroanalysis--. |

Signed and Sealed this
Second Day of October, 2012

David J. Kappos

David J. Kappos
*Director of the United States Patent and Trademark Office*

| | | |
|---|---|---|
| (Item 56) Title Page 8 Col. 1 | 18 | Under Other Publications, change “termistor” to --thermistor--. |
| (Item 56) Title Page 8 Col. 1 | 19 | Under Other Publications, change “metobolites,” to --metabolites,--. |
| (Item 56) Title Page 8 Col. 1 | 21 | Under Other Publications, change “cholesteral and cholesteral” to --cholesterol and cholesterol--. |
| (Item 56) Title Page 8 Col. 2 | 10 | Under Other Publications, change “Subcutaenous” to --Subcutaneous--. |
| (Item 56) Title Page 8 Col. 2 | 22 | Under Other Publications, change “Aced” to --Acad--. |
| (Item 56) Title Page 8 Col. 2 | 36 | Under Other Publications, change “pancrease” to --pancreas--. |
| (Item 56) Title Page 8 Col. 2 | 50 | Under Other Publications, change “Deabetes” to --Diabetes--. |
| (Item 56) Title Page 8 Col. 2 | 54 | Under Other Publications, change “TURNERet” to --TURNER et--. |
| (Item 56) Title Page 9 Col. 1 | 46 | Under Other Publications, change “17(1)25-31.” to --17(1):25-31.--. |
| (Item 56) Title Page 9 Col. 2 | 5 | Under Other Publications, change “Aniodic” to --Anodic--. |
| 3 | 67 | Change “of a” to --of an--. |
| 4 | 38 | Change “andrenostenedione;” to --androstenedione;--. |
| 4 | 53 | Change “diptheria/” to --diphtheria/--. |
| 4 | 60 | Change “perioxidase;” to --peroxidase;--. |
| 5 | 2 | Change “sissomicin;” to --sisomicin;--. |
| 5 | 6 | Change “duodenalisa,” to --duodenalis,--. |
| 5 | 14 | Change “Trepenoma pallidium,” to --Treponema pallidum,--. |
| 5 | 15 | Change “stomatis” to --stomatitis--. |
| 5 | 36 | Change “(barbituates,” to --(barbiturates,--. |
| 8 | 55 | Change “conductimetric,” to --conductometric,--. |
| 9 | 46 | Change “(2H+),” to --($2H^+$),--. |
| 9 | 46 | Change “(2e-),” to --($2e^-$),--. |

| | | |
|---|---|---|
| 11 | 1 | Before “U.S. Pat. No. 5,985,129” delete “to”. |
| 13 | 36 | Change “finctions” to --functions--. |